(12) United States Patent
Ruppersberg

(10) Patent No.: US 11,839,445 B2
(45) Date of Patent: *Dec. 12, 2023

(54) SYSTEMS, DEVICES, COMPONENTS AND METHODS FOR DETECTING THE LOCATIONS OF SOURCES OF CARDIAC RHYTHM DISORDERS IN A PATIENT'S HEART

(71) Applicant: Ablacon Inc., Wheat Ridge, CO (US)

(72) Inventor: Peter Ruppersberg, Blonay (CH)

(73) Assignee: ABLACON, INC., Wheat Ridge, CO (US)

( * ) Notice: Subject to any disclaimer, the term of this patent is extended or adjusted under 35 U.S.C. 154(b) by 47 days.

This patent is subject to a terminal disclaimer.

(21) Appl. No.: 17/212,789

(22) Filed: Mar. 25, 2021

(65) Prior Publication Data
US 2021/0378512 A1 Dec. 9, 2021

Related U.S. Application Data

(63) Continuation of application No. 16/231,883, filed on Dec. 24, 2018, now Pat. No. 10,980,418, which is a (Continued)

(30) Foreign Application Priority Data

Sep. 7, 2015 (WO) .................. PCT/EP2015/001801
Sep. 7, 2015 (WO) .................. PCT/EP2015/001803

(51) Int. Cl.
*A61B 5/00* (2006.01)
*A61B 18/14* (2006.01)
(Continued)

(52) U.S. Cl.
CPC ............ *A61B 5/0006* (2013.01); *A61B 5/287* (2021.01); *A61B 5/316* (2021.01); *A61B 5/327* (2021.01);
(Continued)

(58) Field of Classification Search
CPC .. A61B 5/6852; A61B 5/6858; A61B 18/1492
See application file for complete search history.

(56) References Cited

U.S. PATENT DOCUMENTS 6,301,496 B1 * 10/2001 Reisfeld ................ A61B 5/341
600/407
10,143,374 B2 * 12/2018 Ruppersberg .......... A61B 5/327
(Continued)

FOREIGN PATENT DOCUMENTS

ES       2706537 B2      8/2020
WO    2019/063861 A1    4/2019

OTHER PUBLICATIONS

Rios-Munoz et al., Real-time Rotational Activity Detection in Atrial Fibrillation. Front Physiol. Mar. 13, 2018;9:208 (1-17).
(Continued)

*Primary Examiner* — Eric D. Bertram
(74) *Attorney, Agent, or Firm* — McDermott Will & Emery LLP

(57) ABSTRACT

Disclosed are various examples and embodiments of systems, devices, components and methods configured to detect a location of a source of at least one cardiac rhythm disorder in a patient's heart. In some embodiments, electrogram signals am acquired from inside a patient's heart, and subsequently normalized, adjusted and/or filtered, followed by generating a two-dimensional (2D) spatial map, grid or representation of the electrode positions, processing the amplitude-adjusted and filtered electrogram signals to generate a plurality of three-dimensional electrogram surfaces corresponding at least partially to the 2 D grid, one surface being generated for each or selected discrete times, and processing the plurality of three-dimensional electrogram surfaces through time to generate a velocity vector map corresponding at least partially to the 2 D grid. The resulting velocity vector map is configured to reveal the location of
(Continued)

the source of the at least one cardiac rhythm disorder, which may be, by way of example, an active rotor in a patient's myocardium and atrium.

19 Claims, 22 Drawing Sheets

Related U.S. Application Data continuation of application No. 15/548,671, filed as application No. PCT/IB2016/001273 on Sep. 7, 2016, now Pat. No. 10,201,277.

(51) Int. Cl.
| | |
|---|---|
| A61B 5/287 | (2021.01) |
| A61B 5/316 | (2021.01) |
| A61B 5/327 | (2021.01) |
| A61B 5/339 | (2021.01) |
| A61B 5/341 | (2021.01) |
| A61B 18/00 | (2006.01) |
| A61B 90/00 | (2016.01) |

(52) U.S. Cl.
CPC .............. *A61B 5/339* (2021.01); *A61B 5/341* (2021.01); *A61B 5/6852* (2013.01); *A61B 5/6858* (2013.01); *A61B 5/742* (2013.01); *A61B 18/1492* (2013.01); *A61B 2018/00267* (2013.01); *A61B 2018/00351* (2013.01); *A61B 2018/00577* (2013.01); *A61B 2018/1467* (2013.01); *A61B 2090/065* (2016.02)

(56) References Cited

U.S. PATENT DOCUMENTS

| | | | |
|---|---|---|---|
| 10,201,277 B2* | 2/2019 | Ruppersberg | ........ A61B 5/6858 |
| 10,806,343 B2* | 10/2020 | Ruppersberg | .......... A61B 5/316 |
| 10,820,800 B2* | 11/2020 | Ruppersberg | .......... A61B 5/742 |
| 10,888,236 B2* | 1/2021 | Ruppersberg | ........ A61B 5/6858 |
| 10,980,418 B2* | 4/2021 | Ruppersberg | .......... A61B 5/341 |
| 11,291,395 B2* | 4/2022 | Ruppersberg | ........ A61B 5/7203 |
| 11,389,102 B2* | 7/2022 | Haeusser | .............. A61B 5/4857 |
| 2015/0057522 A1* | 2/2015 | Nguyen | ................. A61B 5/061 |
| | | | 600/374 |
| 2015/0313491 A1* | 11/2015 | Edwards | ................. G16Z 99/00 |
| | | | 600/509 |
| 2017/0027465 A1* | 2/2017 | Blauer | ................. A61B 5/6858 |

OTHER PUBLICATIONS

Rios-Munoz, Rotor Detection in Atrial Fibrillation. Doctoral Thesis. Universidad Carlos III de Madrid. Jun. 2018 159 pages.

* cited by examiner

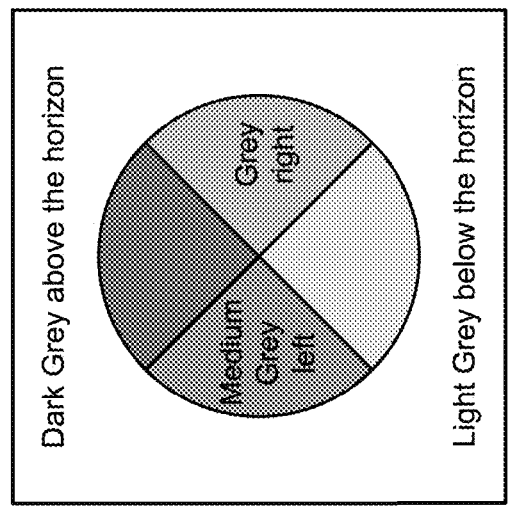
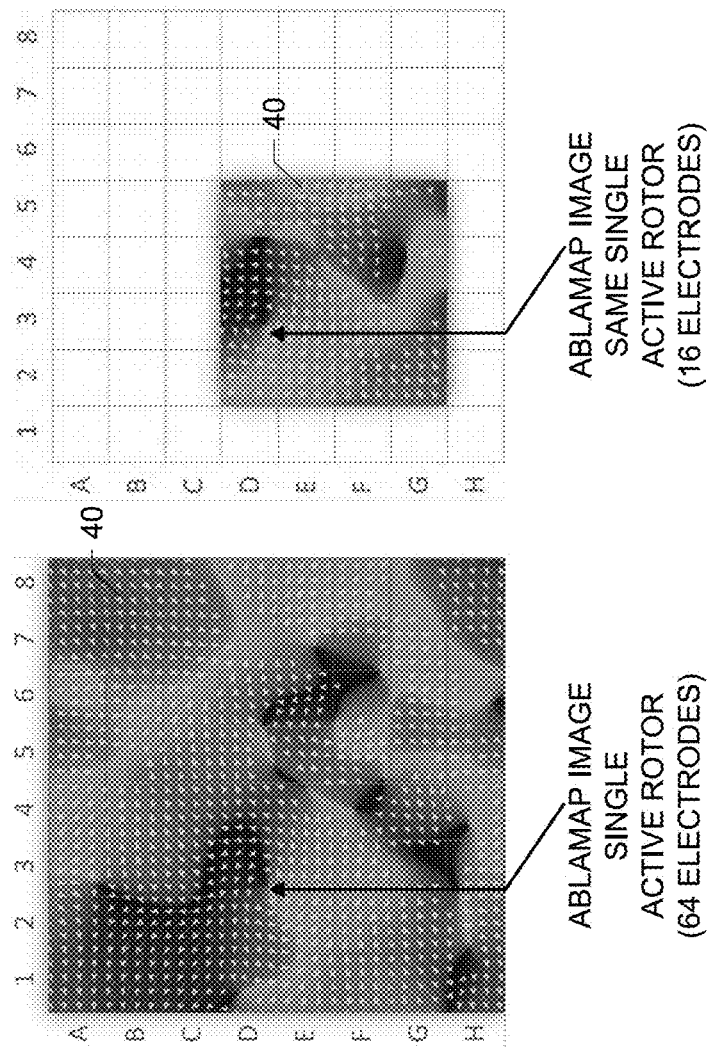
FIG. 10(a) FIG. 10(b) FIG. 10(c)

SYSTEMS, DEVICES, COMPONENTS AND METHODS FOR DETECTING THE LOCATIONS OF SOURCES OF CARDIAC RHYTHM DISORDERS IN A PATIENT'S HEART

PRIORITY, BENEFITS AND CROSS-REFERENCES TO RELATED APPLICATIONS

This patent application is a continuation application of parent U.S. patent application Ser. No. 16/231,883 filed on Dec. 24, 2018 entitled "Systems, Devices, Components and Methods for Detecting the Locations of Sources of Cardiac Rhythm Disorders in a Patient's Heart" to Dr. Peter Ruppersberg ("the '883 parent patent application", now U.S. Pat, No. 10,980,418) and claims priority and other benefits therefrom. The '883 parent patent application is hereby incorporated by reference herein, in its entirety, to provide continuity of disclosure.

This patent application also claims priority and other benefits through the '883 parent patent application to the following applications. U.S. patent application Ser. No. 15/548,671 filed on Aug. 3, 2017 entitled "Systems, Devices, Components and Methods for Detecting the Locations of Sources of Cardiac Rhythm Disorders in a Patient's Heart" to Dr. Peter Ruppersberg ("the '671 patent application," now U.S. Pat. No. 10,201,277), of which the '883 parent patent application is a continuation, and which is also a 371 of: (b) International Patent Application PCT/IB2016/001273 to Ruppersberg filed on. Sep. 7, 2016 entitled "Systems, Device, Components and Methods for Detecting the Locations of Sources of Cardiac Rhythm Disorders in a Patient's Heart (hereafter "the '001273 patent application"); (c) International Patent Application PCT/EP2015/001801 to Ruppersberg filed on Sep. 7, 2015 entitled "Elongated Medical Device Suitable for Intravascular Insertion and Method of Making an Elongated Medical Device Suitable for Intravascular Insertion" (hereafter "the '001801 patent application"), and (d) International Patent Application PCT/EP2015/001803 to Ruppersberg filed on Sep. 7, 2015 entitled "Elongated Medical Device Suitable for Intravascular Insertion and Method of Making an Elongated Medical Device Suitable for Intravascular Insertion" (hereafter the '001803 patent application"). The respective entireties of the '671, '001273, '001801, and '001803 patent applications are also hereby incorporated by reference herein to provide continuity of disclosure.

FIELD OF THE INVENTION

Various embodiments described and disclosed herein relate to the field of medicine generally, and more particularly to diagnosing and treating cardiac rhythm disorders in a patient's heart using electrophysiological mapping techniques, as well as in some embodiments using imaging, navigation, cardiac ablation and other types of medical systems, devices, components, and methods. Various embodiments described and disclosed herein also relate to systems, devices, components and methods for discovering with enhanced precision the location(s) of the source(s) of different types of cardiac rhythm disorders and irregularities in a patient's heart, such as, by way of example, active rotors, passive rotors, areas of fibrosis, breakthrough points and focus points.

BACKGROUND

Persistent atrial fibrillation (AF) is assumed to be caused by structural changes in atrial tissue, which can manifest themselves as multiwavelet re-entry and/or stable rotor mechanisms (see, e.g., De Groot M S at al., "Electropathological Substrate of Longstanding Persistent Atrial Fibrillation in Patients with Structural Heart Disease Epicardial Breakthrough," Circulation, 2010, 3: 1674-1682). Radio frequency (RF) ablation targeting such host drivers of AF is generally accepted as the best therapeutic approach. RF ablation success rates in treating AF cases are currently limited, however, by a lack of diagnostic tools that are capable of precisely determining the source (or type), and location, of such AF drivers. Better diagnostic tools would help reduce the frequency and extent of cardiac ablation procedures to the minimum amount required to treat AF, and would help balance the benefits of decreased fibrillatory burden against the morbidity of increased lesion load.

One method currently employed to localize AF drivers is the TOPERA® RhythmView® system, which employs a basket catheter having 64 electrodes arranged in an 8×8 pattern from which the system records unipolar electrograms or electrogram signals (ECMs). The RhythmView® algorithm creates a propagation map of the 84 electrodes through a phase analysis of EGM peaks after improving the signal to noise ratio through filtering and subtraction of a simulated compound ECG artifact. The RhythmView® algorithm detects where peak sequences between electrodes show a circular pattern candidate for a re-entry cycle and indicates those locations in a Focal Impulse and Rotor Map (FiRM) using A1 to H8 chess field coordinates for the electrodes. The resolution of the TOPERA system is limited by the spacing of the electrodes and consequently does not show the details of the AF drivers. In particular, the TOPERA system cannot show if a circular EGM wavefront is actively generated by a re-entry mechanism and is therefore is a driver of AF (i.e., an active rotor), or whether a circular EGM wavefront simply represents turbulence passively generated by an EGM wavefront hitting a barrier (i.e., a passive rotor). In addition, the TOPERA system does not show the direction of AF wavefront propagation, and does not provide the spatial or temporal resolution required to detect singularities associated with the generation of an active rotor.

A recent independent multicenter study ("OASIS, Impact of Rotor Ablation in Non-Paroxysmal AF Patients: Results from a Randomized Trial", Sanghamitra Mohanty, et al. and Andrea Natale, J Am Col I Cardiol. 2016) reported that the results obtained using TOPERA FIRM technology were inferior to those provided by non-specific ablation of the posterior wall of the left atrium. Moreover, the results suggested that FIRM based ablation is not sufficient for therapeutic success without pulmonary vein isolation (PVI) being performed in parallel. Although there are some questions about the methodology of this trial, many experts are convinced that the resolution and interpretability of the TOPERA system need to be improved.

In another approach to the problem, Toronto scientists recently presented a strategy to analyze EGM wave propagation using "Omnipolar Mapping," which seeks to measure beat by beat conduction velocity and direction (see, e.g., "Novel Strategy for Improved Substrate Mapping of the Atria: Omnipolar Catheter and Signal Processing Technology Assesses Electrogram Signals Along Physiologic and Anatomic Directions," D. Curtis Deno et al. and Kumaraswamy Nanthakumar; Circulation, 2015, 132:A19778). This approach starts with the time derivative of a unipolar EGM as measured by a set of electrodes having known distances to one other. Assuming constant velocity, the velocity and direction representing the best fit for a spatial derivative of the measured EGM are calculated and used to represent an estimate of the E field. According to a communication by Dr. Nanthakumar at the 2016 CardioStim Convention in Nice, France, however, this method remains incapable of dealing successfully with complex data sets, such as those obtained during an episode of AF.

What is needed are improved means and methods of acquiring and processing intracardiac electrogram signals that reliably and accurately yield the precise locations and sources of cardiac rhythm disorders in a patient's heart. Doing so would enable cardiac ablation procedures to be carried out with greater locational precision, and would result in higher rates of success in treating cardiac rhythm disorders such as AF.

Accordingly, it is one objective of the present invention to provide an improved system, especially a medical system, and methods for acquiring and processing intracardiac electrogram signals that reliably and accurately yield the precise locations and sources of cardiac rhythm disorders in a patient's heart.

SUMMARY

In one embodiment, there is provided a system for detecting in a patient's heart a location of a source of at least one cardiac rhythm disorder, the system comprising at least one computing device comprising at least one non-transitory computer readable medium configured to store instructions executable by at least one processor to perform a method of determining the source and location of the cardiac rhythm disorder in the patient's heart, the computing device being configured to: (a) receive electrogram signals, (b) normalize or adjust amplitudes of the electrogram signals; (c) assign predetermined positions of the electrodes on a mapping electrode assembly to their corresponding electrogram signals; (c) provide or generate a two-dimensional (2 D) spatial map of the electrode positions; (d) for discrete or selected times over which the electrogram signals are being processed, process the amplitude-adjusted electrogram signals to generate a plurality of three-dimensional electrogram surfaces corresponding at least partially to the 2D map, one surface being generated for each such time, and (e) process the plurality of three-dimensional electrogram surfaces through time to generate a velocity vector map corresponding at least partially to the 2D map, the velocity vector map being configured to reveal the location of the source of the at least one cardiac rhythm disorder.

In another embodiment, there is provided a method of detecting a location of a source of at least one cardiac rhythm disorder in a patient's heart, the method comprising normalizing or adjusting the amplitudes of electrogram signals acquired from electrodes, especially configured to be located inside the patient's heart, assigning positions or identifiers for each of the electrodes to corresponding individual electrogram signals, providing or generating a two-dimensional (2D) spatial map of the electrode positions, for each or selected discrete times over which the electrogram signals are being processed, processing the amplitude-adjusted electrogram signals to generate a plurality of three-dimensional electrogram surfaces corresponding at least partially to the 2D map, one surface being generated for each such time, and processing the plurality of three-dimensional electrogram surfaces through time to generate a velocity vector map corresponding at least partially to the 2D map, the velocity vector map being configured to reveal the location of the source of the at least one cardiac rhythm disorder.

Electrogram signals and processed data may be delivered or communicated to the system for performing the method, e.g., via a data carrier, after they have been acquired by the electrodes and stored for later processing by the system and method according to this invention. Further advantageous embodiments of the system and method are disclosed herein or will become apparent to those skilled in the art after having read and understood the claims, specification and drawings hereof.

BRIEF DESCRIPTION OF THE DRAWINGS

Different aspects of the various embodiments will become apparent from the following specification, drawings and claims in which:

FIGS. 10(a) through 10(d) show further results obtained using actual patient data.

The drawings are not necessarily to scale. Like numbers refer to like parts or steps throughout the drawings.

DETAILED DESCRIPTIONS OF SOME EMBODIMENTS

Described herein are various embodiments of systems, devices, components and methods for aiding in the diagnosis and treatment cardiac rhythm disorders in a patient's heart using electrophysiological mapping techniques, as well as imaging, navigation, cardiac ablation and other types of medical systems, devices, components, and methods. Various embodiments described and disclosed herein also relate to systems, devices, components and methods for discovering with enhanced precision the location(s) of the source(s)

of different types of cardiac rhythm disorders and irregularities. Such cardiac rhythm disorders and irregularities, include, but are not limited to, arrhythmias, atrial fibrillation (AF or A-fib), atria tachycardia, atrial flutter, paroxysmal fibrillation, paroxysmal flutter, persistent fibrillation, ventricular fibrillation (V-fib), ventricular tachycardia, atrial tachycardia (A-tach), ventricular tachycardia (V-tach), supraventricular tachycardia (SVT), paroxysmal supraventricular tachycardia (PSVT), Wolff-Parkinson-White syndrome, bradycardia, sinus bradycardia, ectopic atrial bradycardia, junctional bradycardia, heart blocks, atrioventricular block, idioventricular rhythm, areas of fibrosis, breakthrough points, focus points, re-entry points, premature atrial contractions (PACs), premature ventricular contractions (PVCs), and other types of cardiac rhythm disorders and irregularities.

Systems and methods configured to detect in a patient's heart a location of a source of at least one cardiac rhythm disorder are disclosed herein. In the following description, for the purposes of explanation, numerous specific details are set forth in order to provide a thorough understanding of example embodiments or aspects. It will be evident, however, to one skilled in the art that an example embodiment may be practiced without necessarily using all of the disclosed specific details.

Figure 1A:
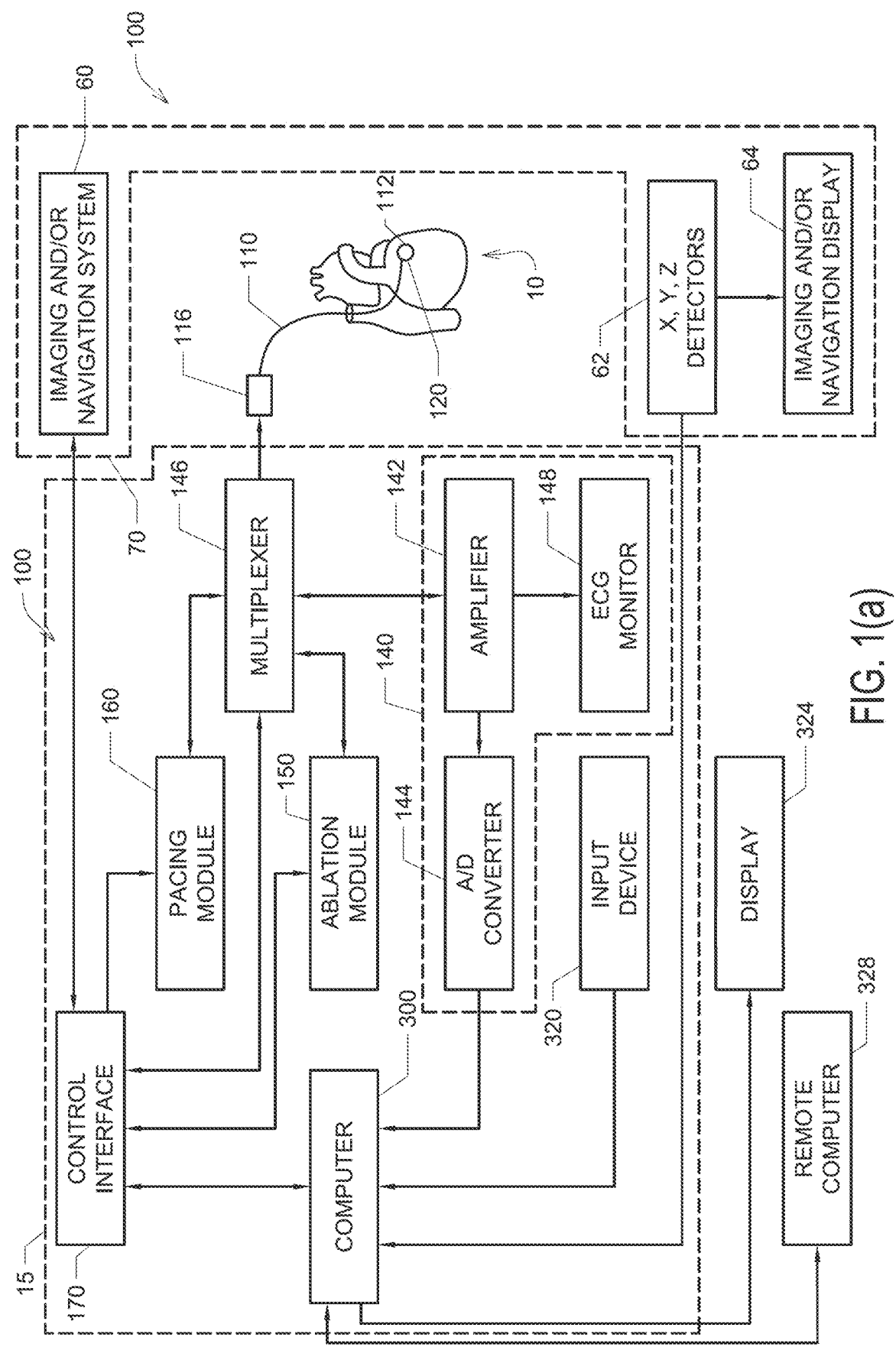
FIG. 1(a) shows one embodiment of a combined cardiac electrophysiological mapping (EP), pacing and ablation system 100.

Referring now to FIG. 1(a), there is illustrated one embodiment of a combined cardiac electrophysiological (EP) mapping, pacing and ablation system 100. Note that in some embodiments system 100 may not include ablation module 150 and/or pacing module 160. Among other things, the embodiment of system 100 shown in FIG. 1(a) is configured to detect and reconstruct cardiac activation information acquired from a patient's heart relating to cardiac rhythm disorders and/or irregularities, and is further configured to detect and discover the location of the source of such cardiac rhythm disorders and/or irregularities with enhanced precision relative to prior art techniques. In some embodiments, system 100 is further configured to treat the location of the source of the cardiac rhythm disorder or irregularity, for example by ablating the patient's heart at the detected location.

The embodiment of system 100 shown in FIG. 1(a) comprises five main functional units electrophysiological mapping (EP mapping) unit 140 (which is also referred to herein as data acquisition device 140), ablation module 150, pacing module 160, imaging and/or navigation system 70, and computer or computing device 300. In one embodiment, at least one computer or computing device or system 300 is employed to control the operation of one or more of systems, modules and devices 140, 150, 160, 170 and 70. Alternatively, the respective operations of systems, modules or devices 140, 150, 160, 170 and 70 may be controlled separately by each of such systems, modules and devices, or by some combination of such systems, modules and devices.

Computer or computing device 300 may be configured to receive operator inputs from an input device 320 such as a keyboard, mouse and/or control panel. Outputs from computer 300 may be displayed on display or monitor 324 or other output devices (not shown in FIG. 1(a)) Computer 300 may also be operably connected to a remote computer or analytic database or server 328. At least each of components, devices, modules and systems 60, 110, 140, 146, 148, 150, 170, 300, 324 and 328 may be operably connected to other components or devices by wireless (e.g., Bluetooth) or wired means. Data may be transferred between components, devices, modules or systems through hardwiring, by wireless means, or by using portable memory devices such as USB memory sticks.

During electrophysiological (EP) mapping procedures, multi-electrode catheter 110 is typically introduced percutaneously into the patient's heart 10. Catheter 110 is passed through a blood vessel (not shown), such as a femoral vein or the aorta, and thence into an endocardial site such as the atrium or ventricle of the head 10.

It is contemplated that other catheters, including other types of mapping or EP catheters, lasso catheters, pulmonary vein isolation (PVI) ablation catheters (which can operate in conjunction with sensing lasso catheters), ablation catheters, navigation catheters, and other types of EP mapping catheters such as EP monitoring catheters and spiral catheters may also be introduced into the heart, and that additional surface electrodes may be attached to the skin of the patient to record electrocardiograms (ECGs).

When system 100 is operating in an EP mapping mode, multi-electrode catheter 110 functions as a detector of intra-electrocardiac signals, while optional surface electrodes may serve as detectors of surface ECGs. In one embodiment, the analog signals obtained from the intracardiac and/or surface electrodes are routed by multiplexer 146 to data acquisition device 140, which comprises an amplifier 142 and an A/D converter (ADC) 144. The amplified or conditioned electrogram signals may be displayed by electrocardiogram (ECC) monitor 148. The analog signals are also digitized via ADC 144 and input into computer 300 for data processing, analysis and graphical display.

In one embodiment, catheter 110 is configured to detect cardiac activation information in the patient's heart 10, and to transmit the detected cardiac activation information to data acquisition device 140, either via a wireless or wired connection. In one embodiment that is not intended to be limiting with respect to the number, arrangement, configuration, or types of electrodes, catheter 110 includes a plurality of 64 electrodes 82, probes and/or sensors A1 through H8 arranged in an 8×8 grid that are included in electrode mapping assembly 120, which is configured for insertion into the patient's heart through the patient's blood vessels and/or veins. Other numbers, arrangements, configurations and types of electrodes 82 in catheter 110 are, however, also contemplated. In most of the various embodiments, at least some electrodes, probes and/or sensors included in catheter 110 are configured to detect cardiac activation or electrical signals, and to generate electrocardiograms or electrogram signals, which are then relayed by electrical conductors from or near the distal end 112 of catheter 110 to proximal end 116 of catheter 110 to data acquisition device 140.

Note that in some embodiments of system 100, multiplexer 146 is not employed for various reasons, such as sufficient electrical conductors being provided in catheter 110 for all electrode channels, or other hardware design considerations. In other embodiments, multiplexer 146 is incorporated into catheter 110 or into data acquisition device 140.

In one embodiment, a medical practitioner or health care professional employs catheter 110 as a roving catheter to locate the site of the location of the source of a cardiac rhythm disorder or irregularity in the endocardium quickly and accurately, without the need for open-chest and open-heart surgery. In one embodiment, this is accomplished by using multi-electrode catheter 110 in combination with real-time or near-real-time data processing and interactive display by computer 300, and optionally in combination with imaging and/or navigation system 70. In one embodiment, multi-electrode catheter 110 deploys at least a two-dimensional array of electrodes against a site of the endocardium at a location that is to be mapped, such as through the use of a Biosense Webster® PENTARAY® EP mapping catheter. The intracardiac or electrogram signals detected by the catheter's electrodes provide data sampling of the electrical activity in the local site spanned by the array of electrodes.

In one embodiment, the electrogram signal data are processed by computer 300 to produce a display showing the locations(s) of the source(s) of cardiac rhythm disorders and/or irregularities in the patient's heart 10 in real-time or near-real-time, further details of which are provided below. That is, at and between the sampled locations or the patient's endocardium, computer 300 may be configured to compute and display in real-time or near-real-time an estimated, detected and/or determined location(s) of the site(s), source(s) or origin)s) of the cardiac rhythm disorder(s) and/or irregularity(s) with in the patient's heart 10. This permits a medical practitioner to move interactively and quickly the electrodes 82 of catheter 110 towards the location of the source of the cardiac rhythm disorder or irregularity.

In some embodiments of system 100, one or more electrodes, sensors or probes detect cardiac activation from the surface of the patient's body as surface ECGs, or remotely without contacting the patient's body (e.g., using magnetocardiograms). In another example, some electrodes, sensors or probes may derive cardiac activation information from echocardiograms. In various embodiments of system 100, external or surface electrodes, sensors and/or probes can be used separately or in different combinations, and further may also be used in combination with intracardiac electrodes, sensors and/or probes inserted within the patient's heart 10. Many different permutations and combinations of the various components of system 100 are contemplated having, for example, reduced, additional or different numbers of electrical sensing and other types of electrodes, sensors and/or transducers.

Continuing to refer to FIG. 1(*a*), EP mapping system or data acquisition device 140 is configured to condition the analog electrogram signals delivered by catheter 110 from electrodes 82 A1 through H8 in amplifier 142. Conditioning of the analog electrogram signals received by amplifier 142 may include, but is not limited to, low-pass filtering, high-pass filtering, bandpass filtering, and notch filtering. The conditioned analog signals are then digitized in analog-to-digital converter (ADC) 144. ADC 144 may further include a digital signal processor (DSP) or other type of processor which is configure to further process the digitized electrogram signals (e.g., low-pass filter, high-pass filter, bandpass filter, notch filter, automatic gain control, amplitude adjustment or normalization, artifact removal, etc.) before they are transferred to computer or computing device 300 for further processing and analysis.

As discussed above, in some embodiments, multiplexer 146 is separate from catheter 110 and data acquisition device 140, and in other embodiments multiplexer 146 is combined in catheter 110 or data acquisition device 140.

In some embodiments, the rate at which individual electrogram and/or ECO signals are sampled and acquired by system 100 can range between about 0.25 milliseconds and about 8 milliseconds, and may be about 0.5 milliseconds, about 1 millisecond, about 2 milliseconds or about 4 milliseconds. Other sample rates are also contemplated. While in some embodiments system 100 is configured to provide unipolar signals, in other embodiments system 100 is configured to provide bipolar signals.

In one embodiment, system 100 can include a BARD® LABSYSTEM™ PRO EP Recording System, which is a computer and software driven data acquisition and analysis tool designed to facilitate the gathering, display, analysis, pacing, mapping, and storage of intracardiac EP data. Also in one embodiment, data acquisition device 140 can include a BARD® CLEAR-SIGN™ amplifier, which is configured to amplify and condition electrocardiographic signals of biologic origin and pressure transducer input, and transmit such information to a host computer (e.g., computer 300 or another computer).

As shown in FIG. 1(*a*), and as described above, in some embodiments system 100 includes ablation module 150, which may be configured to deliver RF ablation energy through catheter 110 and corresponding ablation electrodes disposed near distal end 112 thereof, and/or to deliver RF ablation energy through a different catheter (not shown in FIG. 1(*a*)). Suitable ablation systems and devices include, but are not limited to, cryogen ic ablation devices and/or systems, radiofrequency ablation devices and/or systems, ultrasound ablation devices and/or systems, high-intensity focused ultrasound (HIFU) devices and/or systems, chemical ablation devices and/or systems, and laser ablation devices and/or systems.

When system 100 is operating in an optional ablation mode, multi-electrode catheter 110 fitted with ablation electrodes, or a separate ablation catheter, is energized by ablation module 150 under the control of computer 300, control interface 170, and/or another control device or module. For example, an operator may issue a command to ablation module 150 through input device 320 to computer 300. In one embodiment, computer 300 or another device controls ablation module 150 through control interface 170. Control of ablation module 150 can initiate the delivery of a programmed series of electrical energy pulses to the endocardium via catheter 110 (or a separate ablation catheter, not shown in FIG. 1(*a*)). One embodiment of an ablation method and device is disclosed in U.S. Pat. No. 5,383,917 to Desai et al., the entirety of which is hereby incorporated by reference herein.

In an alternative embodiment, ablation module 150 is not control led by computer 300, and is operated manually directly under operator control. Similarly, pacing module 160 may also be operated manually directly under operator control. The connections of the various components of system 100 to catheter 110, to auxiliary catheters, or to surface electrodes may also be switched manually or using multiplexer 146 or another device or module.

When system 100 is operating in an optional pacing mode, multi-electrode catheter 110 is energized by pacing module 160 operating under the control of computer 300 or another control device or module. For example, an operator may issue a command through input device 320 such that computer 300 controls pacing module 160 through control interface 170, and multiplexer 146 initiates the delivery of a programmed series of electrical simulating pulses to the endocardium via the catheter 110 or another auxiliary catheter (not shown in FIG. 1(*a*)). One embodiment of a pacing module is disclosed in M. E. Josephson et al., in "VENTRICULAR ENDOCARDIAL PACING II, The Role of Pace Mapping to Localize Origin of Ventricular Tachycardia," The American Journal of Cardiology, vol. 50, November 1982.

Computing device or computer 300 is appropriately configured and programmed to receive or access the electrogram signals provided by data acquisition device 140. Computer 300 is further configured to analyze or process such electrogram signals in accordance with the methods, functions and logic disclosed and described herein so as to permit reconstruction of cardiac activation information from the electrogram signals. This, in turn, makes it possible to locate with at least some reasonable degree of precision the location of the source of a heart rhythm disorder or irregularity. Once such a location has been discovered, the source may be eliminated or treated by means that include, but are not limited to cardiac ablation.

In one embodiment, and as shown in FIG. 1(a), system 100 also comprises a physical imaging and/or navigation system 70. Physical imaging and/or navigation device 60 included in system 70 may be, by way of example, a 2- or 3-axis fluoroscope system, an ultrasonic system, a magnetic resonance imaging (MRI) system, a computed tomography (CT) imaging system, and/or an electrical impedance tomography EIT) system. Operation of system 70 be controlled by computer 300 via control interface 170, or by other control means incorporated into or operably connected to imaging or navigation system 70. In one embodiment, computer 300 or another computer triggers physical imaging or navigation system 60 to take "snap-shot" pictures of the heart 10 of a patient (body not shown). A picture image is detected by a detector 62 along each axis of imaging, and can include a silhouette of the head as well as a display of the inserted catheter 110 and its electrodes 82 A1-H8 (more about which is said below), which is displayed on imaging or navigation display 64. Digitized image or navigation data may be provided to computer 300 for processing and integration into computer graphics that are subsequently displayed on monitor or display 64 and/or 324.

In one embodiment, system 100 further comprises or operates in conjunction with catheter or electrode position transmitting and/or receiving coils or antennas located at or near the distal end of an EP mapping catheter 110, or that of an ablation or navigation catheter 110, which are configured to transmit electromagnetic signals for intra-body navigational and positional purposes.

In one embodiment, imaging or navigation system 70 is used to help identify and determine the precise two- or three-dimensional positions of the various electrodes included in catheter 110 with in patient's heart 10, and is configured to provide electrode position data to computer 300. Electrodes, position markers, and/or radio-opaque markers can be located on various portions of catheter 110, mapping electrode assembly 120 and/or distal end 112, or can be configured to act as fiducial markers for imaging or navigation system 70.

Medical navigation systems suitable for use in the various embodiments described and disclosed herein include, but are not limited to, image-based navigation systems, model-based navigation systems, optical navigation systems, electromagnetic navigation systems (e.g. B1 OSENSE® WEBSTER® CARTO® system), and impedance-based navigation systems (e.g., the St. Jude® ENSITE™ VELOCITY™ cardiac mapping system), and systems that combine attributes from different types of imaging AND navigation systems and devices to provide navigation with in the human body (e.g., the MEDTRONIC® STEALTHSTATION® system).

In view of the structural and functional descriptions provided herein, those skilled in the art will appreciate that portions of the described devices and methods may be configured as methods, data processing systems, or computer algorithms. Accordingly, these portions of the devices and methods described herein may take the form of a hardware embodiment, a software embodiment, or an embodiment combining software and hardware, such as shown and described with respect to computer system 300 illustrated in FIG. 1(b). Furthermore, portions of the devices and methods described herein may be a computer algorithm stored in a computer-usable storage medium having computer readable program code on the medium. Any suitable computer-readable medium may be utilized including, but not limited to, static and dynamic storage devices, hard disks, optical storage devices, and magnetic storage devices.

Certain embodiments of portions of the devices and methods described herein are also described with reference to block diagrams of methods, systems, and computer algorithm products. It will be understood that such block diagrams, and combinations of blocks diagrams in the Figures, can be implemented using computer-executable instructions. These computer-executable instructions may be provided to one or more processors of a general purpose computer, a special purpose computer, or any other suitable programmable data processing apparatus (or a combination of devices and circuits) to produce a machine, such that the instructions, which executed via the processor(s), implement the functions specified in the block or blocks of the block diagrams.

These computer-executable instructions may also be stored in a computer-readable memory that can direct computer 300 or other programmable data processing apparatus to function in a particular manner, such that the instructions stored in the computer-readable memory result in an article of manufacture including instructions which implement the function specified in an individual block, plurality of blocks, or block diagram. The computer program instructions may also be loaded onto computer 300 or other programmable data processing apparatus to cause a series of operational steps to be performed on the computer or other programmable apparatus to produce a computer implemented process such that the instructions which execute on computer 300 or other programmable apparatus provide steps for implementing the functions specified in an individual block, plurality of blocks, or block diagram.

Figure 1B:
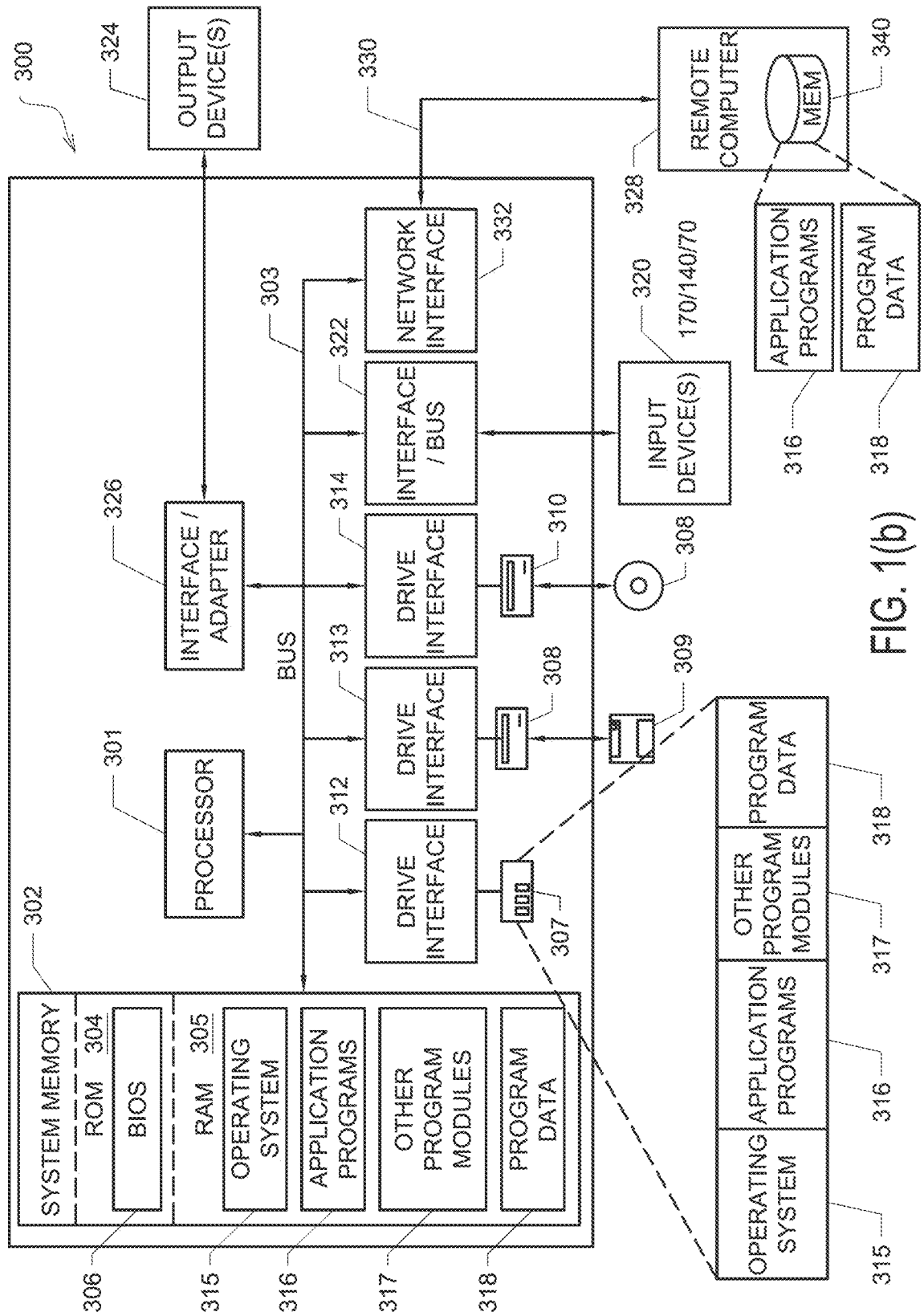
FIG. 1(b) shows one embodiment of a computer system 300.

In this regard. FIG. 1(b) illustrates only one example of a computer system 300 (which, by way of example, can include multiple computers or computer workstations) that can be employed to execute one or more embodiments of the devices and methods described and disclosed herein, such as devices and methods configured to acquire and process sensor or electrode data, to process image data, and/or transform sensor or electrode data and image data associated with the analysis of cardiac electrical activity and the carrying out of the combined electrophysiological mapping and analysis of the patient heart 10 and ablation therapy delivered thereto.

Computer system 300 can be implemented on one or more general purpose computer systems or networked computer systems, embedded computer systems, routers, switches, server devices, client devices, various intermediate devices/ nodes or standalone computer systems. Additionally, computer system 300 or portions thereof may be implemented on various mobile devices such as, for example, a personal digital assistant (PDA), a laptop computer and the like, provided the mobile device includes sufficient processing capabilities to perform the required functionality.

In one embodiment, computer system 300 includes processing unit 301 (which may comprise a CPU, controller, microcontroller, processor, microprocessor or any other suitable processing device), system memory 302, and system bus 303 that operably connects various system components, including the system memory, to processing unit 301. Multiple processors and other multi-processor architectures also can be used to form processing unit 301. System bus 303 can comprise any of several types of suitable bus architectures, including a memory bus or memory controller, a peripheral bus, or a local bus. System memory 302 can include read only memory (ROM) 304 and random access memory (RAM) 305. A basic input/output system (BIOS) 306 can be stored in ROM 304 and contain basic routines configured to transfer information and/or date among the various elements within computer system 300.

Computer system 300 can include a hard disk drive 303, a magnetic disk drive 308 (e.g., to read from or write to removable disk 309), or an optical disk drive 310 (e.g., for reading CD-ROM disk 311 or to read from or write to other optical media). Hard disk drive 303, magnetic disk drive 308, and optical disk drive 310 are connected to system bus 303 by a hard disk drive interface 312, a magnetic disk drive interface 313, and an optical drive interface 314, respectively. The drives and their associated computer-readable media are configured to provide nonvolatile storage of data, data structures, and computer-executable instructions for computer system 300. Although the description of computer-readable media above refers to a hard disk, a removable magnetic disk and a CD, other types of media that are readable by a computer, such as magnetic cassettes, flash memory cards, digital video disks and the like, in a variety of forms, may also be used in the operating environment; further, any such media may contain computer-executable instructions for implementing one or more parts of the devices and methods described and disclosed herein.

A number of program modules may be stored in drives and RAM 303, including operating system 315, one or more application programs 316, other program modules 313, and program data 318. The application programs and program data can include functions and methods programmed to acquire, process and display electrical data from one or more sensors, such as shown and described herein. The application programs and program data can include functions and methods programmed and configured to process data acquired from a patient, e.g. for assessing heart function, such as shown and described herein with respect to FIGS. 1-10(f).

A health care provider or other user may enter commands and information into computer system 300 through one or more input devices 320, such as a pointing device (e.g., a mouse, a touch screen, etc.), a keyboard, a microphone, a joystick, a game pad, a scanner, and the like. For example, the user can employ input device 320 to edit or modify the data being input into a data processing algorithm (e.g., only data corresponding to certain time intervals). These and other input devices 320 may be connected to processing unit 301 through a corresponding input device interface or port 322 that is operably coupled to the system bus, but may be connected by other interfaces or ports, such as a parallel port, a serial port, or a universal serial bus (USB). One or more output devices 324 (e.g., display, a monitor, a printer, a projector, or other type of display device) may also be operably connected to system bus 303 via interface 326, such as through a video adapter.

Computer system 300 may operate in a networked environment employing logical connections to one or more remote computers, such as remote computer 328. Remote computer 328 may be a workstation, a computer system, a router, or a network node, and may include connections to many or all the elements described relative to computer system 300. The logical connections, schematically indicated at 330, can include a local area network (LAN) and/or a wide area network (WAN).

When used in a LAN networking environment, computer system 300 can be connected to a local network through a network interface or adapter 332. When used in a WAN networking environment, computer system 300 may include a modem, or may be connected to a communications server on the LAN. The modem, which may be internal or external, can be connected to system bus 303 via an appropriate port interface. In a networked environment, application programs 316 or program data 318 depicted relative to computer system 300, or portions thereof, may be stored in a remote memory storage device 340.

Figure 2:
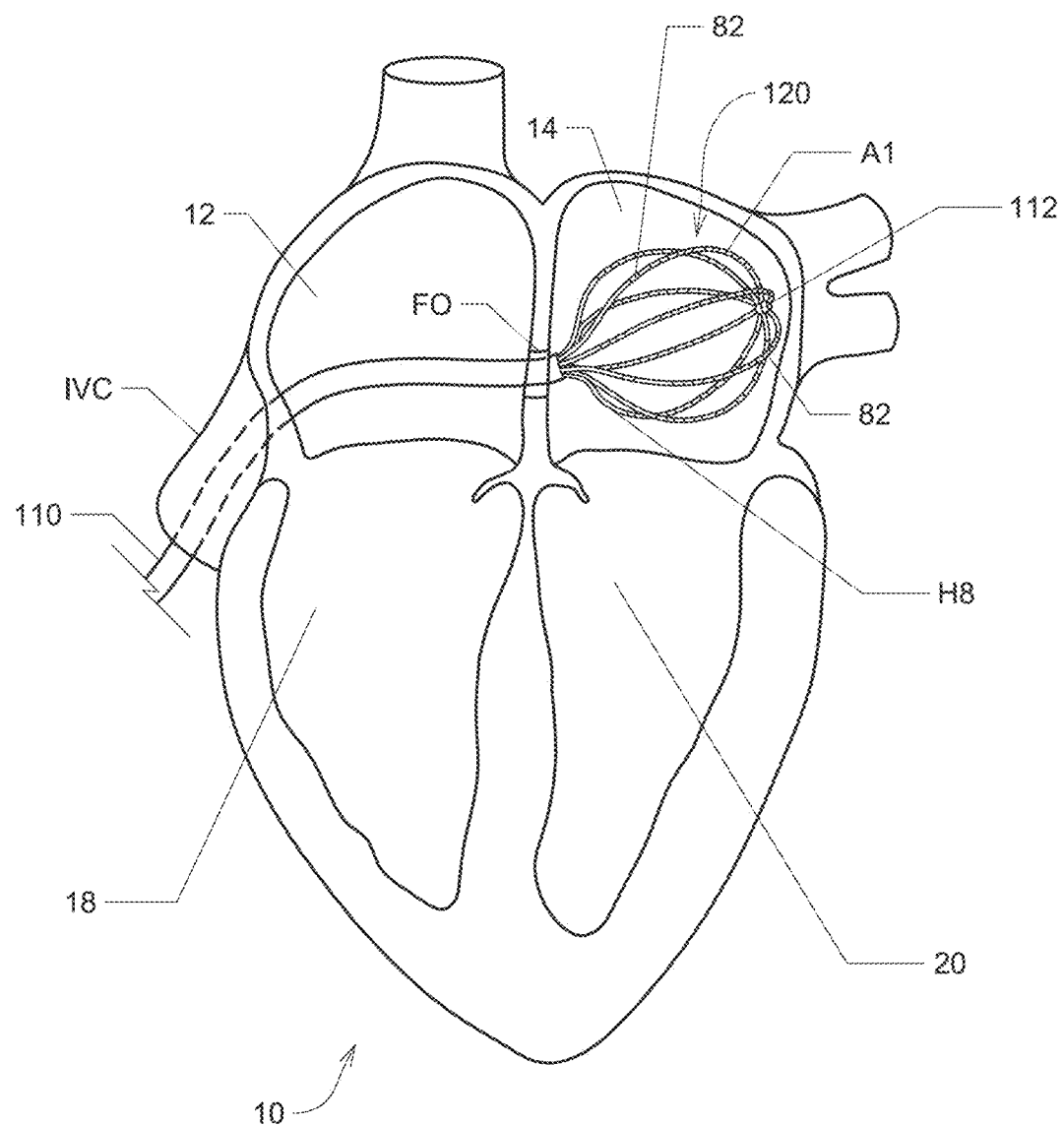
FIG. 2 shows an illustrative view of one embodiment of a distal portion of catheter 110 inside a patient's left atrium 14.

Referring now to FIG. 2, there is shown an illustrative view of one embodiment of a distal portion of catheter 110 inside a patient's left atrium 14. As shown in FIG. 2, heart 10 includes right atrium 12, left atrium 14, right ventricle 18, and left ventricle 20. Mapping electrode assembly 120 is shown in an expanded or open state inside left atrium 13 after it has been inserted through the patient's inferior vena cava and foramen ovalene ("IVC" and "FO" in FIG. 2), and is configured to obtain electrogram signals from left atrium 12 via an 8×8 array of electrodes 82 A1 through H8. Mapping electrode assembly and catheter 110 may also be positioned with the patient's right atrium 12, left ventricle 18 and right ventricle 20.

Figure 3:
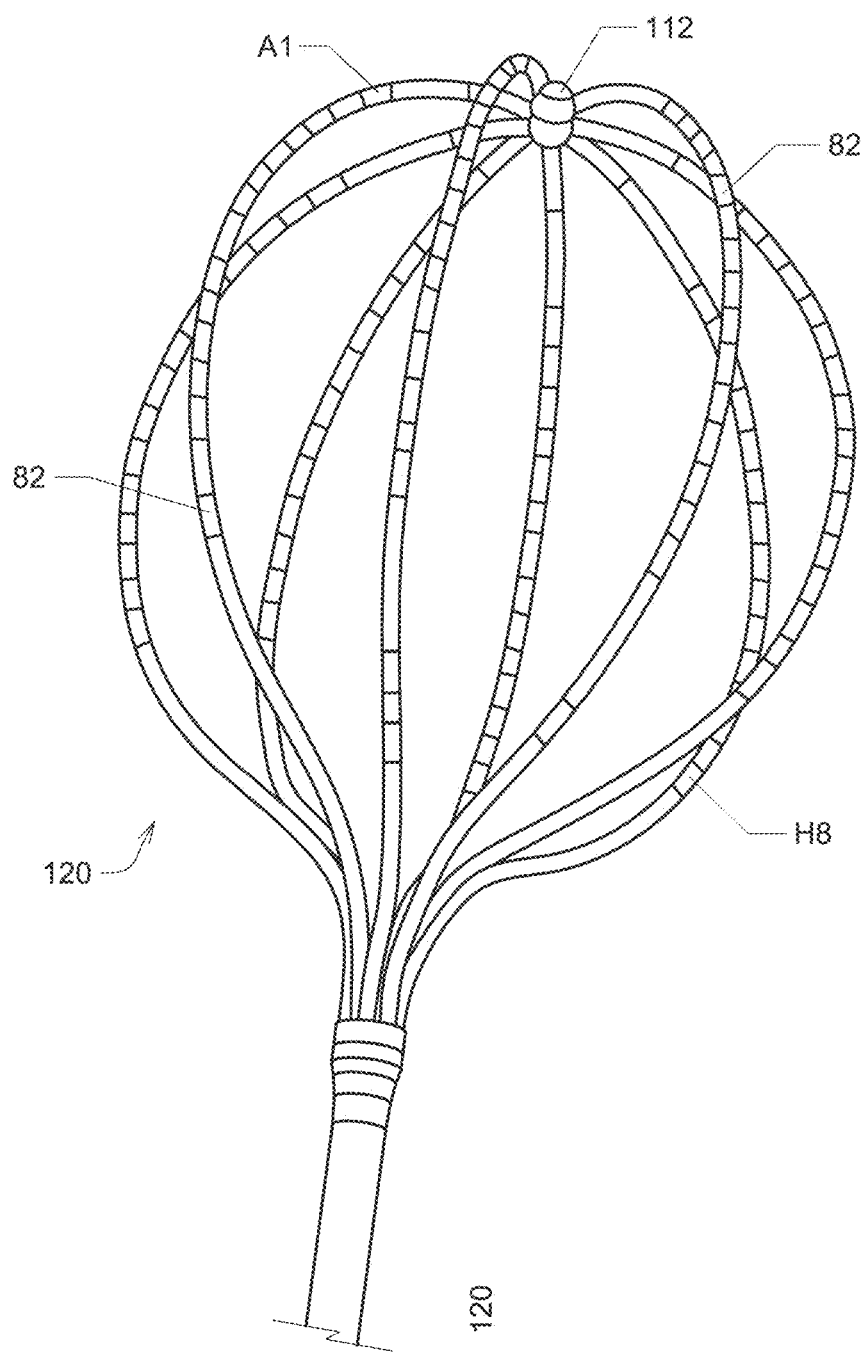
FIG. 3 shows an illustrative embodiment of a mapping electrode assembly 120 of catheter 110 of FIG. 2.

FIG. 3 shows an illustrative embodiment of a mapping electrode assembly 120, which in FIG. 3 forms a distal portion of a Boston Scientific® CONSTELLATION® full contact mapping catheter. The CONSTELLATION EP catheter permits full-contact mapping of a patient's heart chamber, and may also be employed to facilitate the assessment of entrainment, conduction velocity studies, and refractory period in a patient's heart 10. Mapping electrode assembly 120 shown in FIG. 3 permits the simultaneous acquisition of longitudinal and circumferential signals for more accurate 3-D mapping, and features a flexible basket design that conforms to atrial anatomy and aids aid in accurate placement. Sixty-four electrodes 82 A1 through H8 can provide comprehensive, real-time 3-D information over a single heartbeat.

Figure 4:
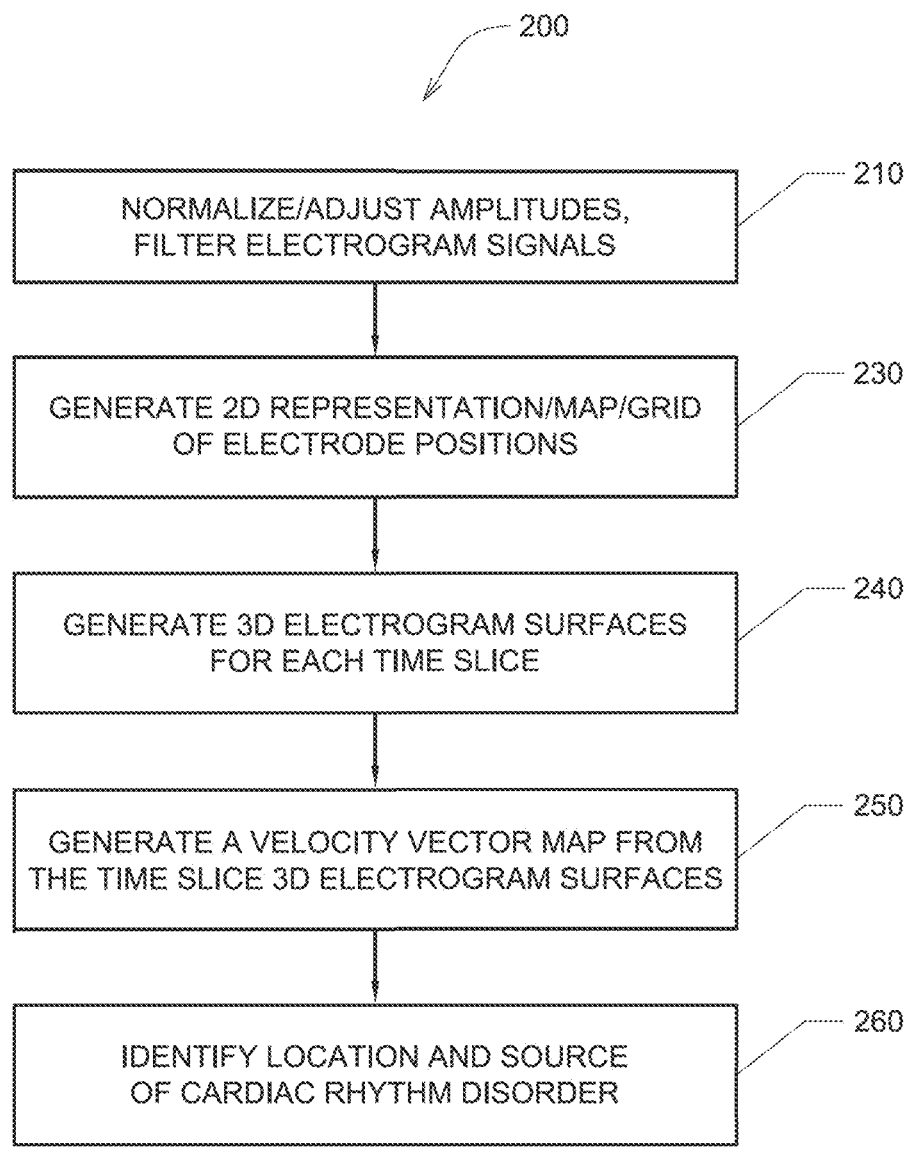
FIG. 4 shows one embodiment of an algorithm or method 200 of detecting a location of a source of at least one cardiac rhythm disorder in a patient's heart.

FIG. 4 shows one embodiment of a method 200 of detecting a location of a source of at least one cardiac rhythm disorder in a patient's heart. At step 210, the amplitudes of electrogram signals acquired from electrodes 82 located inside a patient's heart. e.g., electrodes 82 included in a mapping electrode assembly 120, ae normalized and/or adjusted. At step 230, positions A1 through H8 corresponding to each of the electrodes 82 of mapping electrode assembly 120 are assigned to the individual electrogram signals that have been acquired. At step 230, a two-dimensional (2 D) spatial map of electrode positions A1 through H8 is generated or provided. In some embodiments, a three-dimensional (3 D) spatial map of electrode positions A1 through H8 is generated or provided. (As discussed above, fewer or more than 64 electrodes 82 may be used to measure electrogram signals and/or surface ECCs, and electrode arrays other than 8×8 or rectangular grids are contemplated in the various embodiments.)

For discrete or selected times over which the electrogram signals are being analyzed and processed, at step 240 the amplitude-adjusted electrogram signals are processed across the 2D (or 3D) map to generate a plurality of three-dimensional electrogram surfaces (which according to one embodiment may be smoothed electrogram surfaces), one surface being generated for each such discrete time. At step 250, the plurality of three-dimensional electrogram surfaces that have been generated across the 2D (or 3D) map through time are processed to generate a velocity vector map. The velocity vector map is configured to reveal the location of the source of the at least one cardiac rhythm disorder. In a subsequent optional step (not shown in FIG. 4), method 200 further comprises ablating patient's heart 10 at the location of the source of the cardiac rhythm disorder indicated by the velocity vector map.

Algorithm 200 outlined in FIG. 4 presents one embodiment of a method of processing electrogram signals provided by one or more mapping catheters so as to transform time domain waveform information into space domain information, and then calculate velocity vector maps that correspond to normalized space potential profile movements for each point in space. For reasons that are explained below, algorithm 200 has the advantages that it is robust against artifacts and provides a virtual resolution that is higher than the actual electrode density employed to acquire the EP mapping data through the use of a fitting algorithm that determines the most likely mean spatial velocity map derived from hundreds of individual samples of amplitude patterns recorded by the mapping electrodes.

As described above, in step 210 of FIG. 4 the amplitudes of electrogram signals acquired from electrodes located inside the patient's heart are normalized or otherwise adjusted. In step 240, the amplitude-adjusted electrogram signals are processed across a 2D or 3D map to generate a plurality of three-dimensional electrogram surfaces, one surface being generated for each such discrete time. In one embodiment, the resulting individual time-slice surfaces can be strung together sequentially to provide a time-varying depiction of electrical activation occurring over the portion of the patient's heart that has been monitored. According to embodiments that have been discovered to be particularly efficacious in the field of intracardiac EP monitoring and data processing and analysis, at least portions of the electrogram surfaces we found to correspond to estimated wave shapes, and are generated using Green's function, which in some embodiments, and by way of non-limiting example, may be combined with two- or three-dimensional bi-harmonic spline interpolation functions to generate such surfaces.

In one embodiment, electrogram signal date acquired from the patient's heart 10 are not equidistantly sampled. For example, in one such embodiment, electrogram signal data acquired from the patient's heart 10 are not equidistantly sampled by mapping electrode assembly 120, and instead are assigned their respective chessboard locations A1 through H8 as approximations of electrode locations in a cylindrical 20 projection of a grid representative of the interior surface of the patient's heart that is being mapped. In many applications, it has been discovered that such approximations of electrode locations yield perfectly useable and accurate results when steps 230 through 250 are cared out after steps 210 and 230.

In another embodiment, when superimposing the acquired electrogram signal data onto a 2D or 3D map or grid in step 230, the electrogram signal data may be associated with their actual or more accurately estimated positions in the 2D projection of the grid using positional data provided by for example, imaging or navigation system 70. Resampling of electrogram signals on the grid may also be carried out. Gridding may also be carried out such as by convolution-type filtering, Kriging, and using splines. Most gridding techniques operate on an equidistant grid and solve the equations governing the gridding process with either finite difference or finite element implementations.

One approach that has been discovered to work particularly well with electrogram signal data is to determine the Green's function associated with each electrogram value assigned to a given chessboard location, and then construct the solution as a sum of contributions from each data point, weighted by the Green's function evaluated for each point of separation. Biharmonic spline interpolation, which can be used in conjunction with Green's function, has also been discovered to work especially well in the context of processing and analyzing electrogram signal data. In some embodiments, undesirable oscillations between data points are removed by interpolation with splines in tension based on Green's function. A Green's function technique for Interpolation and surface fitting and generation of electrogram signal data has been found to be superior to conventional finite-difference methods because, among other things, the model can be evaluated at arbitrary x,y locations rather than only on a rectangular grid. This is a very important advantage of using Green's function in step 240, because precise evenly-spaced-apart grid locations, resampling of electrogram signals, and finite-difference gridding calculations are not required to generate accurate representations of electrogram surfaces in step.

In one embodiment, Green's function $G(x; x')$ is employed in step 240 for a chosen spline and geometry to interpolate data at regular or arbitrary output locations. Mathematically, the solution is $w(x) = \text{sum } (c(i) G(x'; x(i)))$, for $i=1, n$, and a number of data points $(x(i), w(i))$. Once the n coefficients $c(i)$ have been calculated, the sum may be evaluated at any output point x. A selection is made between minimum curvature, regularized, or continuous curvature splines in tension for either 1-D, 2-D, or 3-D Cartesian coordinates or spherical surface coordinates. After removing a linear or planar trend (i.e., in Cartesian geometries) or mean values (i.e., spherical surfaces) and normalizing residuals, a least-squares matrix solution for spline coefficients $c(i)$ may be determined by solving the n by n linear system $w(j) = \text{sum-over-i } (c(i) G(x); x(i)))$, for $j=1, n$: this solution yields an exact interpolation of the supplied data points. For further details regarding the algorithms and mathematics underlying Green's function, see: (1) "Moving Surface Spline Interpolation Based on Green's Function." Xingsheng Deng and Zhong-an Tang. Math. Geosci (2011), 43:663680 ("the Deng paper"), and (2) "Interpolation with Splines in Tension: A Green's Function Approach." Paul Wessel and David Bercovici, Mathematical Geology, 77-93, Vol. 30, No. 1, 1998 ("the Wessel paper"). The respective entireties of the Deng and Wessel papers are hereby incorporated by reference herein.

Still further details regarding the use or Green's function in interpolating and generating surfaces may be found in: Interpolation by regularized spline with tension: I, Theory and implementation, Mitasova, H., and L. Miles, 1993, Math. Geol., 25, 641-655: Parker. R. L, 1994, Geophysical Inverse Theory, 386 pp., Princeton Univ. Press. Princeton, N.J.: Sandwell, D. T., 1987, Biharmonic spline interpolation of Geos-3 and Seasat allimeter data, Geophys. Res. Lett., 14, 139-142; Wessel, P., and J. M. Becker, 2008. Interpolation using a generalized Green's function for a spherical surface spine in tension, Geophys. J. Int. 174, 21-28, and Wessel, P., 2009. A general-purpose Green's function interpolator, Computers & Geosciences, 35, 1247-1254. Moving Surface Spline Interpolation Based on Green's Function, Xingsheng Deng. Zhongan Tang, Mathematical Geosciences, August 2011, Volume 43, Issue 6, pp 663-680.

Note, however, that a number of different surface smoothing, surface fitting, surface estimation and/or surface/data interpolation processing techniques may be employed in step 240 of FIG. 4, which are not limited to Green's function, and which include, but are not limited to, inverse distance weighted methods of interpolation, triangulation with linear interpolation, bilinear surface interpolation methods, bivariate surface interpolation methods, cubic convolution interpolation methods. Kriging interpolation methods. Natural Neighbor or "area-stealing" Interpolation methods, spine interpolation techniques (including bi-harmonic spline fitting techniques and "spline with barriers" surface interpolation methods), global polynomial interpolation methods, moving least squares interpolation methods, polynomial least square filing Interpolation methods, simple weighted-average operator interpolation methods, multi-quadric biharmon ic function interpolation methods, and artificial neural network interpolation methods. See, for example: "A brief description of natural neighbor interpolation (Chapter 2)." in V. Barnett. Interpreting Multivariate Data. Chichester: John Wiley, pp, 21-36), and "Surfaces generated by Moving Least Squares Methods," P. Lancaster et al., Mathematics of Computation, Vol. 37. No. 155 Qul., 1981), 141-158).

As described above, in step 250 of FIG. 4, the plurality of three-dimensional electrogram surfaces may be processed across the 2D or 3D map through time to generate a velocity vector map, the velocity vector map being configured to reveal the location of the source of the at least one cardiac rhythm disorder. According to embodiments that have been discovered to be particularly efficacious in the field of intracardiac EP monitoring and subsequent data processing and analysis, at least portions of the velocity vector map are generated using one or more optical flow analysis and estimation techniques and methods. Such optical flow analysis techniques may include one or more of Horn-Schunck, Buxton-Buston, Black-Jepson, phase correlation, block-based, discrete optimization, Lucas-Kanade, and differential methods of estimating optical flow. From among these various optical flow estimation and analysis techniques and methods, however, the Horn-Schunck method has so far been discovered to provide superior results in the context of processing and analyzing cardiac electrogram signals, for reasons that are discussed in further detail below.

Two papers describe the Horn-Schunck method particularly well: (1) "SimpleFlow: A Non-Iterative, Sublinear Optical Flow Algorithm," Michael Tao et al., Eurographics 2012, Vol. 31 (2012), No. 2 ("the Tao paper"), and (2) "Horn-Schunck Optical Flow with a Multi-Scale Strategy," Enric Meinhardt-Llopis et al., Image Processing On Line, 3 (2013), pp. 151-172 ("the Meinhardt-Llopis paper"). The respective entireties of the Tao and Meinhardt-Llopis papers are hereby incorporated by reference herein.

In "Determining Optical Flow," by B. K. P. Horn and B. C. Schunck, Artificial Intelligence, Vol. 17, pp. 185-204, 1981, the entirety of which is also hereby incorporated by reference herein, a method for finding an optical flow pattern is described which assumes that the apparent velocity of a brightness pattern varies smoothly throughout most of an image. The Horn-Schunck algorithm assumes smoothness in flow over most or all of an image. Thus, the Horn-Schunck algorithm attempts to minimize distortions in flow and prefers solutions which exhibit smoothness. The Horn-Schunck method of estimating optical flow is a global method which introduces a global constraint of smoothness to solve the aperture problem of optical flow.

A description of some aspects of conventional application of the Horn-Schunck method is set forth in U.S. Pat. No. 6,480,615 to Sun et al. entitled "Motion estimation with in a sequence of data frames using optical flow with adaptive gradients," the entirety of which is also hereby incorporated by reference herein. As described by Sun et al., the Horn-Schunck computation is based on the observation that flow velocity has two components, and that a rate of change of image brightness requires only one constraint. Smoothness of flow is introduced as a second constraint to solve for optical flow. The smoothness constraint presumes there are no spatial discontinuities. As a result, Horn and Schunck excluded situations where objects in an image occlude or block one another. This is because at object boundaries of an occlusion in an image, discontinuities in reflectance appear.

In conventional optical flow analysis. Image brightness is considered al pixel (x,y) in an image plane at time I to be represented as a function I(x,y,t). Based on initial assumptions that the intensity structures of local time-varying image regions are approximately constant under motion for at least a short duration, the brightness of a particular point in the image is constant, so that dt/dt=0. Based on the chain rule of differentiation, an optical flow constraint equation (I) can be represented as follows:

$$Ix(x,y,t)\cdot u+Iy(x,y,t)\cdot v+It(x,y,t)=0,$$

where
Ix=3I(x,y,t)/9x=horizontal spatial gradient of the image intensity;
Iy=5I(x,y,t)/dy=vertical spatial gradient of the image intensity;
It=dI(x,y,t)/3l=temporal image gradient of the image intensity;
u=dx/dt=horizontal image velocity (or displacement); and
v=dy/dt=vertical image velocity (or displacement).

The above optical flow equation is a linear equation having two unknowns, (i.e., u and v). The component of motion in the direction of the brightness gradient is known to be It(Ix 2+Iy 2)V2. However, one cannot determine the component of movement in the direction of the iso-brightness contours at right angles to the brightness gradient. As a consequence, the optical flow velocity (u,v) cannot be computed locally without introducing additional constraints. Horn and Schunck therefore introduce a smoothness constraint. They argue that if every point of the brightness pattern can move independently, then there is little hope of recovering the velocities. However, if opaque objects of finite size are undergoing rigid motion or deformation, neighboring points on the objects should have similar velocities. Correspondingly, the velocity field of the brightness patterns in the image will vary smoothly almost everywhere.

Advantages of the Horn-Schunck algorithm include that it yields a high density of flow vectors, i.e., the flow information missing in inner parts of homogeneous objects is filled in from the motion boundaries. On the negative side, the Horn-Schunck algorithm can be sensitive to noise.

The foregoing discussion regarding how the Horn-Schunck optical flow technique typically focuses on conventional applications, where the brightness or intensity of an object changes over time (which is where the term "optical flow" is derived from). Here, the brightness or intensity of an object is not the issue at hand. Instead, the amplitudes of electrogram signals, and how they change shape and propagate in time and space over a patient's heart, are sought to be determined. One underlying objective of method or algorithm 200 is to produce a vector velocity map, which is a representation of electrographical flow (and not optical flow) within e.g. a patient's heart. Instead of looking for differences or changes in optical brightness or intensity, changes in the velocity, direction and shape of electrical signals (i.e., changes in electrographical flow) across a patient's heart are determined. That is, algorithm 200 does not process optical measurement data corresponding to intensity or brightness, but processes electrical measurement data corresponding to amplitude, potential shape, and/or voltage. One of the reasons why algorithm 200 works so well in detecting the locations of the sources of cardiac rhythm disorders and irregularities is that ion channels in a patient's heart produce action potential voltages that are relatively constant (except in areas of fibrosis). As described above, the Horn-Schunck method assumes "brightness constancy" as one of its key constraints. The normalized/amplitude-adjusted electrogram signals provided by step 210 help satisfy this key constraint of the Horn-Schunck method so that this method may be applied successfully in step 250.

In addition, because of the stability imparted to electrographical flow solutions determined using the Horn-Schunck method, artifacts and noise are generally low in velocity vector maps generated in step 250. In fact, it is believed that the Horn-Schunck method may generally be applied with greater success to electrographical flow data than to optical data because of the unique nature of action potential signals in the human heart, and the manner in which electrogram signals are processed and conditioned before an optical flow analysis is performed on them as described and disclosed herein.

Algorithm 200 described and disclosed herein also does not employ spatial derivatives of electrical potentials (as is done by Deno et al. and Kumaraswamy Nanthakumar using "omnipolar" signals) or time derivatives of electrogram signals (as is done in the TOPERA system). Time derivatives of signals are known to increase noise. Algorithm 200 has as its key inputs the potentials of electrogram signals (not their derivatives). As a result, algorithm 200 is notably free from the effects of spurious noise and artifacts introduced by time-derivative data processing techniques, including in step 250.

In another embodiment, the velocity vector map or step 250 is generated using the Lucas-Kanade optical flow algorithm, which is a differential method for optical flow estimation developed by Bruce D. Lucas and Takeo Kanade. It assumes that the flow is essentially constant in a local neighbourhood of a pixel under consideration, and solves the basic optical flow equations for all the pixels in that neighborhood using least squares criteria. By combining information from several nearby pixels, the Lucas-Kanade method can often resolve the inherent ambiguity of the optical flow equation. It is also less sensitive to image noise than point-wise methods. On the other hand, since it is a purely local method, it can not provide flow information in the interior of uniform regions of the image. See "An iterative Image Registration Technique with an Application to Stereo Vision," Bruce D. Lucase, Takeo Kanade, Proceedings of Imaging Understanding Workshop, pp. 121-130 (1981), the entirety of which is hereby incorporated by reference herein.

In yet another embodiment, various aspects of the Horn-Schunck and Lucas-Kanade algorithms are combined to yield an optical flow algorithm that exhibits the local methods inherent in Lucas-Kanade techniques and the global methods inherent in the Horn-Schunck approach and its extensions. Often local methods are more robust under noise, while global techniques yield dense flow fields. See, for example, "Lucas/Kanade Meets Horn/Schunck: Combining Local and Global Optic Flow Methods," Andres Bruhn, Joachim Weickert, Christoph Schnorr, International Journal of Computer Vision, February 2005, Volume 61, Issue 3, pp 211-231, the entirety of which is hereby incorporated by reference herein.

Various embodiments of algorithm 200 feature several advantages with respect to prior art systems and methods that generate intracardiac images and attempt to detect the locations of cardiac rhythm disorders or irregularities. A key underlying assumption of signal processing techniques that employ Hilbert Transform, Discrete Fourier Transforms (DFTs) or Fast Fourier Transforms (FFTs) is that the signal to be transformed is periodic. As is well known in the field of digital signal processing, this underlying basic assumption is frequently incorrect, and can lead to problems such as spectral leakage. Contrariwise, in some embodiments of algorithm 200, an underlying assumption is that the electrical activity in a patient's heart is based upon ion channel activation, which is a stochastic and non-periodic process, and so strictly periodic behaviour is not assumed or required in subsequent data processing and manipulation steps.

Indeed, none of steps 210, 230, 240, or 250 of method or algorithm 200 absolutely requires the use of Hilbert or Fourier transforms to process data. Instead, in some embodiments each of these steps can be carried out in the time domain without the need for frequency domain or quadrature conversion. For example, in step 210 the amplitudes of the various traces or electrograms can be normalized or adjusted in the time domain according to a selected standard deviation. In another example, rotors detected by algorithm 200 are not assumed to be singularities in a phase map (as is assumed in techniques based upon frequency domain or Hilbert transform signal processing). This key difference also explains why the rotational direction of a rotor can be revealed or detected accurately by algorithm 200 (and not at all, or very unsatisfactorily, using the frequency domain or Hilbert transforms of other methods employed to detect rotors). Note that in some embodiments, however, Hilbert, DFT and/or FFT signal processing components may be or are included in the data processing flow of algorithm 200 (e.g. DSP filtering, deconvolution, etc.).

Figure 5A:
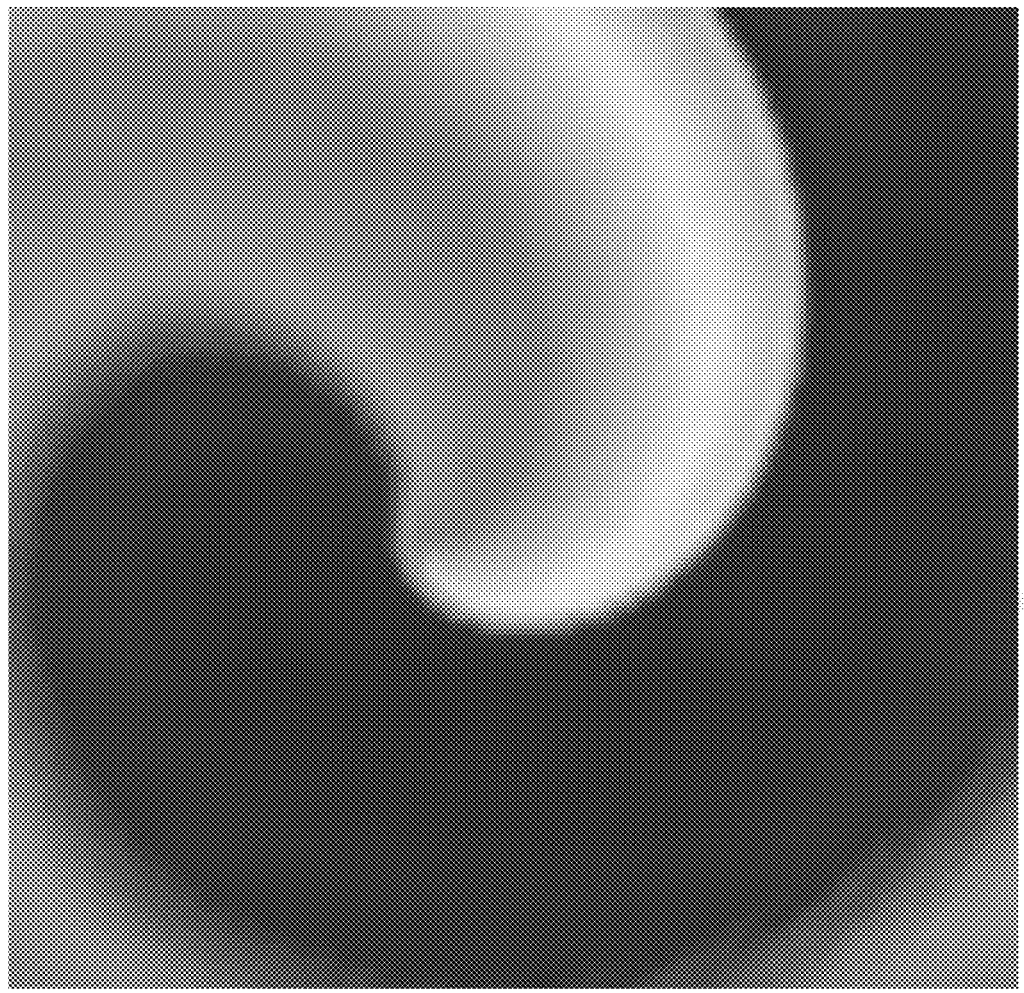
FIG. 5(a) shows a simple rotor model.

Referring now to FIG. 5(a), there is shown a simple rotor model. This model was used to generate simulated ECG signals sensed by an 8×8 array of virtual electrodes. The simple rotor model shown in FIG. 5(a) is from "Chaste: An Open Source C++ Library for Computational Physiology and Biology, Gary R. Mirams, et al. PLOS Computational Biology, Mar. 14, 2013., Vol. 9, issue 3, e1002970, the entirety of which is hereby incorporated by reference herein.

Figure 5B:
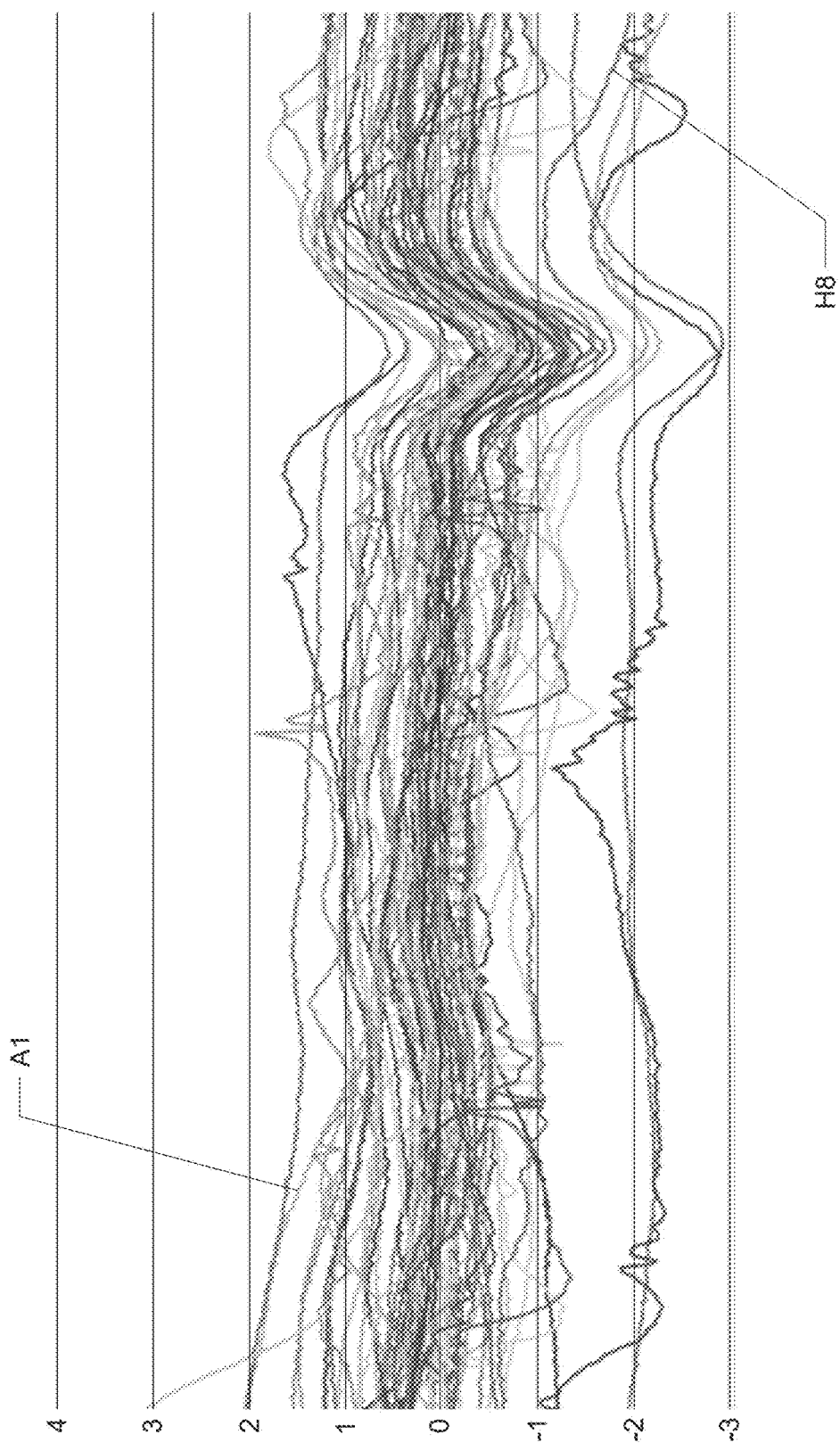
FIG. 5(b) shows sensed artifacts in electrogram signals.

FIG. 5(b) shows artifacts in electrogram signals derived from actual patient data, where 400 msec. traces were recorded using a 64-electrode basket catheter located in the left atrium of a patient suffering from atrial fibrillation. As shown in FIG. 5(b), the sensed artifacts in the electrogram signals include DC offsets of several millivolts that shift with time, a common far-field ventricular depolarization superimposed on the local potentials sensed by individual electrodes, and noise. Moreover, the amplitudes of the various sensed electrogram signals shown in FIG. 5(b) will be seen to vary considerably. These amplitude variations result at least in part on from varying degrees to which individual electrodes touch, or ae physically coupled to, the patients endocardial surface. Electrogram signals corresponding to electrodes in loose, poor or no contact with a patient's endocardium may be an order of magnitude smaller than those where electrodes are well coupled to the endocardial surface.

Figure 5C:
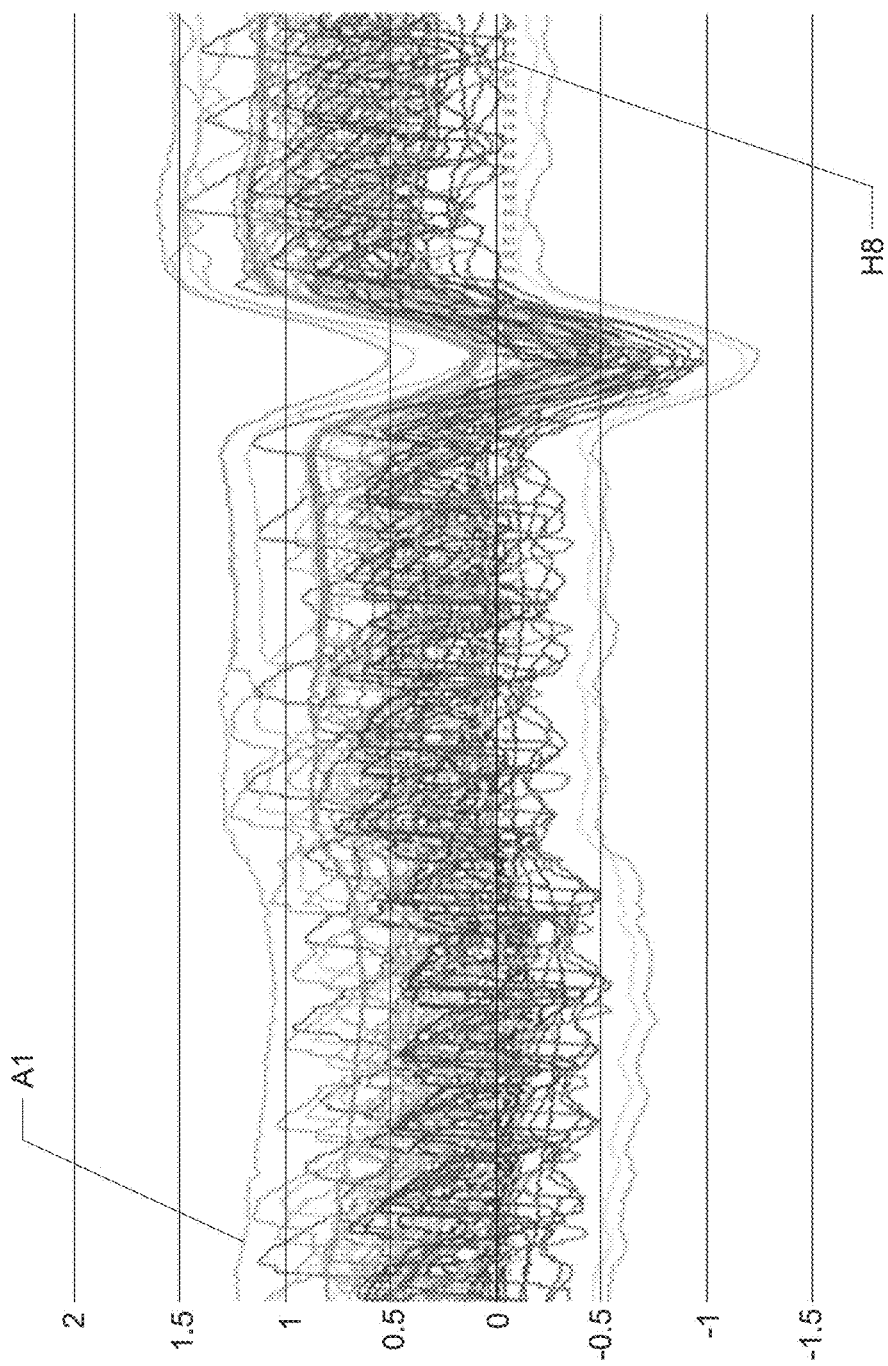
FIG. 5(c) shows the artifacts of FIG. 5(b) superimposed on simulated ECG signals.
Figure 5D:
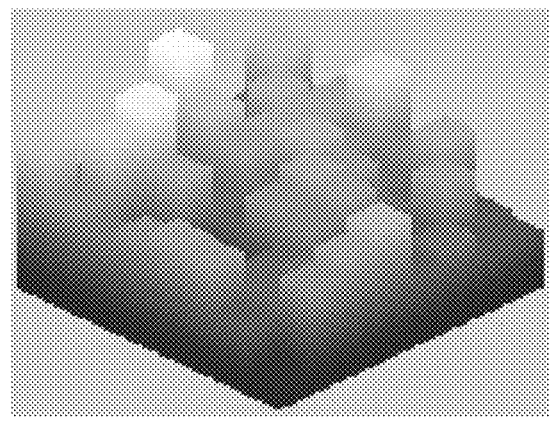
FIG. 5(d) shows a box plot corresponding to an 8×8 array of 64 electrode signals.

FIG. 5(c) shows the artifacts of FIG. 5(b) superimposed on the simulated ECC signals generated from the rotor model of FIG. 5(a). FIG. 5(d) shows a box plot corresponding to the 8×8 array of 64 electrode signals shown in FIG. 5(a) at a selected common time for all traces. Because of the artifacts from FIG. 5(b) introduced into the electrogram signals of FIG. 5(c), the box plot of FIG. 5(d) appears quite irregular and chaotic, and the original spiral shape of the underlying rotor of FIG. 5(a) is not discernable to the eye.

The data shown in FIG. 5(c) were used to perform an analysis in accordance with algorithm 200, which was carried out in three main steps: (1) normalization/adjustment/filtering of electrogram signals (step 210); (2) generating three-dimensional smoothed electrogram surfaces for discrete times or time slices from the normalized/adjusted/filtered electrogram signals (step 240) generated in the first main step 210, and (3) generating a velocity vector map based on the smoothed electrogram surfaces (step 250) generated in the second main step 240.

Figure 5E:
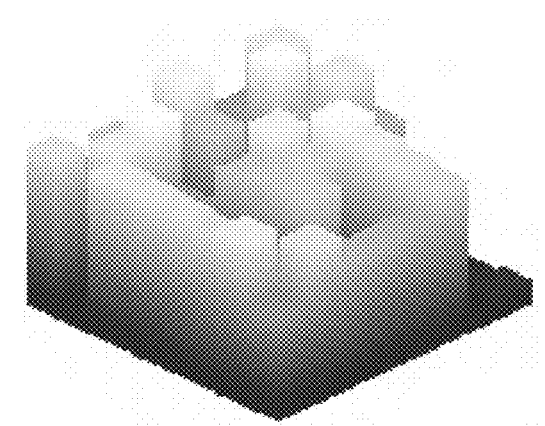
FIG. 5(e) shows the data of FIG. 5(d) after they have been subjected to an electrode signal normalization, adjustment and filtering process.

Described now is one embodiment and illustrative example of the first main step of the algorithm 200 (normalization/adjustment/filtering of electrogram signals). Referring now to FIG. 5(e), there are shown the data of FIG. 5(d) after they have been subjected to one embodiment of an electrode signal normalization, adjustment and filtering process. After normalization and filtering, the simple rotor structure shown in FIG. 5(a) becomes visible in FIG. 5(e). Uniform electrode signal amplitude minima and maxima were first calculated and then applied to individual electrogram signals to generate individual amplitude equalized electrogram signals. Unwanted artifacts such as ventricular depolarization signals were removed from the individual equalized electrogram signals by first averaging all electrogram signals to generate a common electrogram artifact signal, which was then subtracted from each of the equalized individual electrogram signals. The resulting equalized artifact-compensated electrogram signals were then high-pass filtered between 5 and 20 Hz to remove DC offsets from the electrogram signals such that the resulting filtered electrogram signals were approximately zeroed around the X (time) axis. These results are shown in FIG. 5(e).

Next, a sliding time window ranging between about 0.1 seconds and about to 1 second in length was applied to each filtered electrogram signal to generate individual amplitude-adjusted electrogram signals. (In some embodiments, the length of the siding time window corresponds to, or is less then, the slowest repetition frequency expected to be present.) The resulting sliding-window amplitude-adjusted electrogram signals were then stored for later use to generate image backgrounds in velocity vector maps, where they could be used to show low amplitude areas indicative of valve defects/artifacts, loose electrode contact, and/or areas of fibrosis in the patient's myocardium. In the sliding-window amplitude-adjusted electrogram signals, the respective minima and maxima of each position of the sliding time window were used to normalize the amplitude values of all signals between zero and one (or 0 and 255 on an 8-bit integer numeric scale). Because the maximum and minimum values occurred at different time points for electrodes placed in different locations, this process yielded spatial information regarding action potential wave patterns for each sampled time point (more about which is said below).

Now I describe one embodiment and illustrative example of the second main step of the algorithm 200 (generating three-dimensional electrogram surfaces for discrete times or time slices, or estimation of spatial wave shapes). The second step of algorithm 200 takes the spatial distributions of all electrodes 82 and their normalized voltage values at discrete times (e.g., the data represented by the box plots corresponding to selected discrete times with in the selected time window over which electrogram signals were acquired and measured), and estimates or generates from such data or box plots corresponding to given discrete times respective continuous voltage surfaces (or action potential waveform estimates) in space. Because the electrode pattern density is limited, and depending on the method that is used to generate the estimated voltage surfaces, the estimated surfaces typically deviate to some extent from "true" surfaces. Such deviations are usually relatively small in magnitude, however, since the spatial size of the action potential wave given by its velocity [e.g., 0.5 to 1 m/sec.) times the action potential duration (e.g., 0.1 to 0.2 sec.) is much larger (e.g., 0.05 m) than the electrode spacing (e.g., about 1 mm to about 10 mm), and thus spatial aliasing generally does not occur. The electrode grid provided by catheter 110 thus permits relatively good estimates of action potential wave shapes or wavefronts in the form of smoothed electrogram surfaces to be obtained as they propagate across the myocardium. On the other hand, because of the fast sampling rate (which can, for example, range between about 0.25 milliseconds and about 8 milliseconds, and which in some embodiments is nominally about 1 millisecond), changes in the spatial shape or expression of the action potential wavefront from one sample to the next are typically relatively small (e.g., about 1 mm) compared to the electrode distances (which in some embodiments nominally range between about 2 mm and about 7 mm). Thus, algorithm 200 is capable of detecting spatial changes in action potential wavefronts or wave shapes using time domain information (i.e., small amplitude changes between time samples) to estimate changes in the spatial domain (where relatively small shifts in action potentials occur at given electrode measurement locations).

Figure 5F:
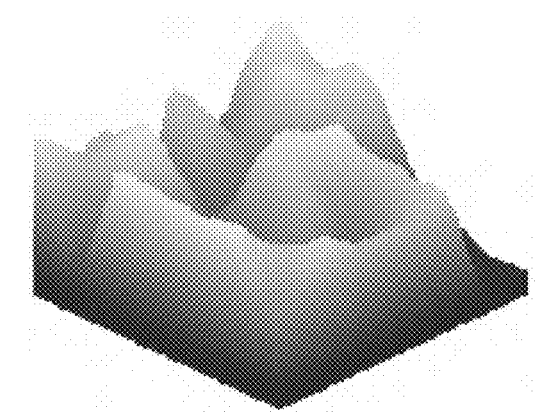
FIG. 5(f) shows a surface generated from the data shown in FIG. 5(e)
Figure 5G:
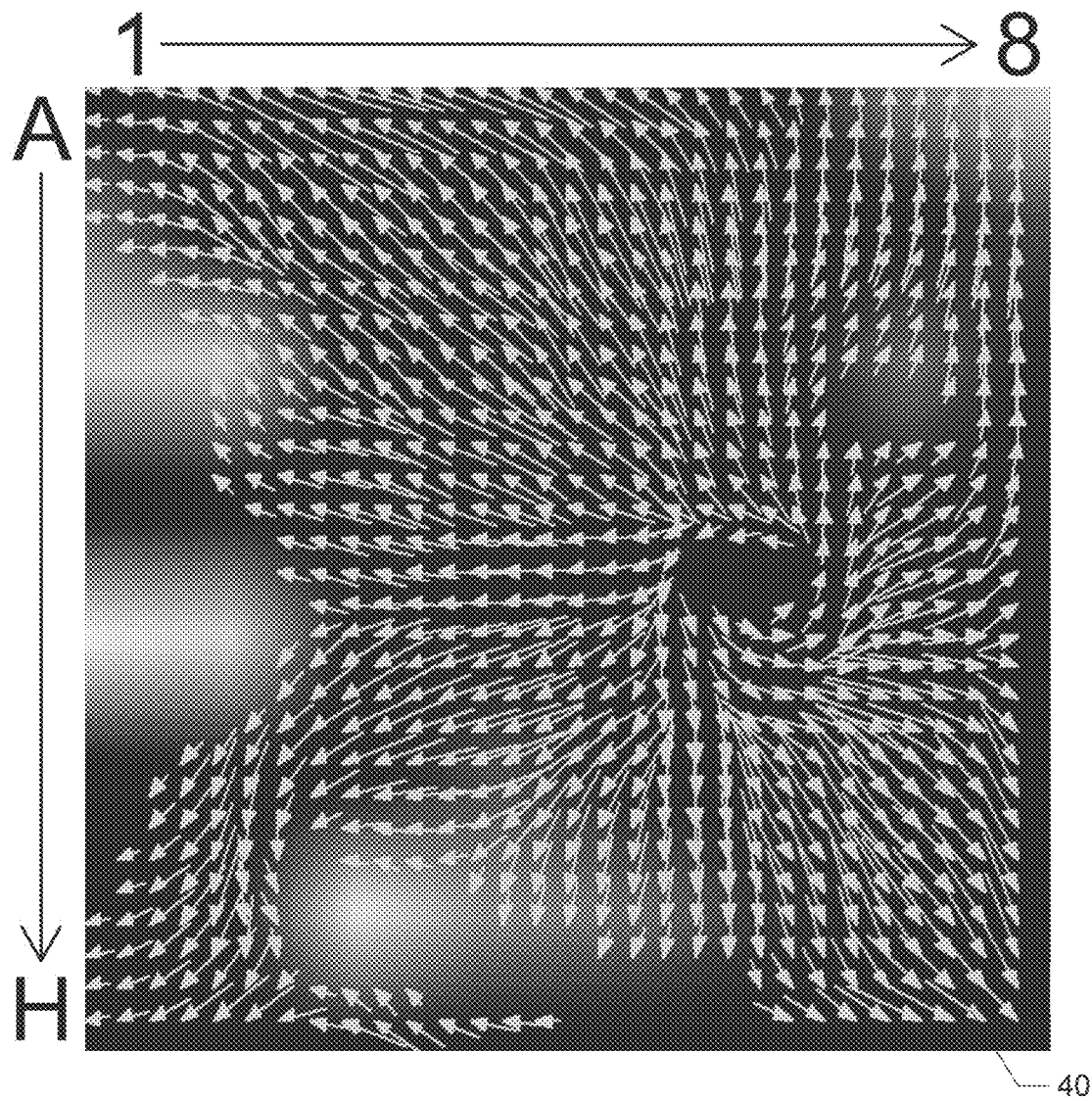
FIG. 5(g) shows wavefront velocity vectors.

One embodiment of a method for estimating action potential wavefronts or wave shapes employs an 8×8 rectangular electrode grid (e.g., TOPERA®-like) model, which operates in two principal steps. First, each electrode/electrogram signal value at a discrete moment n time defines the height of its respective box in the "chess field" box plots shown in FIGS. 5(d) and 5(e). Second, a smoothed electrogram surface is generated for each box plot (or discrete slice of time) by calculating for each horizontal x-y point (typically on a 300×300 grid) an average of neighboring z-values (or electrical potentials) in the box plot. In 3D models that take assumed or actual electrode positions and spacing into account (using, e.g., information from a navigation or imaging system), smoothed electrogram surfaces are generated using 2D bi-harmonic spline interpolation techniques and Green's function. Using the foregoing simple averaging approach, the smoothed electrogram surface of FIG. 5(f) was generated from the data shown in FIG. 5(e). As shown in FIG. 5(f), a spatial wave shape estimate of a rotor appears prominently in the forward center portion of the resulting smoothed surface, which tracks closely the original spiral wave shown in FIG. 3(a).

Described now is one embodiment and illustrative example of the third main step of algorithm 200 (generating a velocity vector map based on the electrogram surfaces). The third main step of algorithm 200 uses the action potential wave shape estimates electrogram surfaces generated at discrete times or time splices provided by the second main step to calculate a velocity vector map. For each sample interval a spatial wave shape or smoothed surface is calculated according to the second main step described above. Since the wave shapes differ only by a small delta between individual samples, and minimum and maximum values are normalized, shift vectors can be calculated at a spatial resolution that is higher than the spatial resolution of the electrodes 82 (e.g., 30×30 samples). Since individual shifts between samples may differ according to random error, a velocity vector fit can be generated using 40 to 100 samples, where an average of observed shift vectors of the action potential wave shape care calculated. If the angle of a rotating wavefront is shifted by a few degrees per sample, the vector arrows 40 will exhibit a circular pattern and in fact can resolve circles that are much smaller than inter-electrode distances. In one embodiment, the third main step of the algorithm employs a vector pattern equation that best fits the observed movement of the evaluated spatial element or wavefront. In one embodiment that has been discovered to provide excellent results, and as described above, the velocity vector map is calculated using the Horn-Schunck optical flow method described above. That is, in one embodiment the Horn-Schunck optical flow method is used in the third main step of algorithm 200 to estimate the velocity and direction of wavefronts or wave shapes between sampled times. Velocities of 40 to 100 samples are typically averaged to yield the most stable results.

FIG. 5(*g*) shows the resulting wavefront velocity vectors indicated by arrows 40) calculated from a series of 60 averaged time slices of smoothed surfaces samples corresponding to the data shown in FIG. 5(*i*). An active rotor is distinctly visible in the right-hand central portion of FIG. 5(*g*), where arrows 40 are flowing tightly in a counterclockwise direction. In FIG. 5(*g*), action potential wavefronts are seen to be moving outwardly away from the detected active rotor (as would be expected in the case of an active rotor)).

Figure 6A:
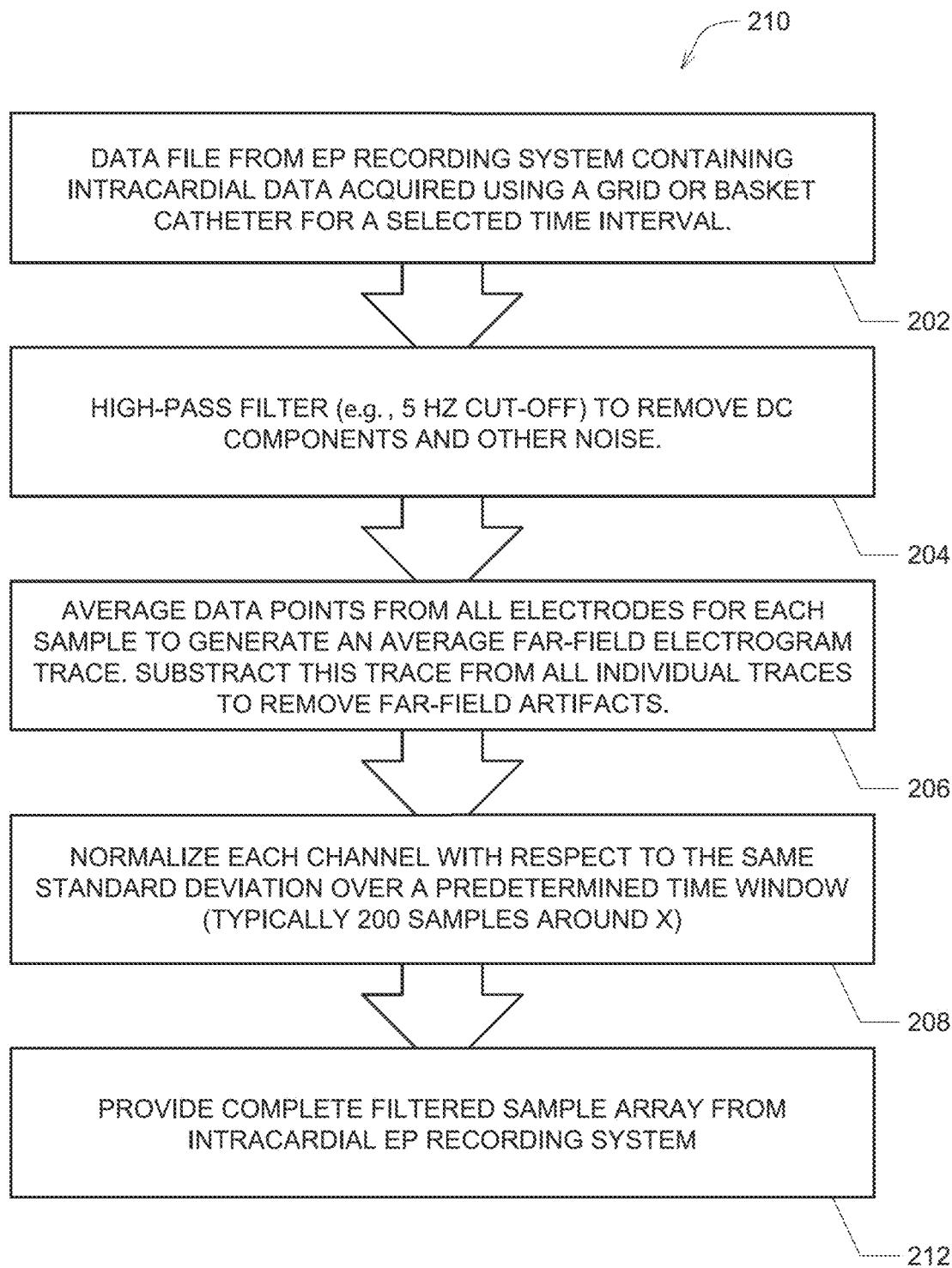
FIGS. 6(a) through 6(c) show details regarding one embodiment of method or algorithm 200 shown in FIG. 4.
Figure 6B:
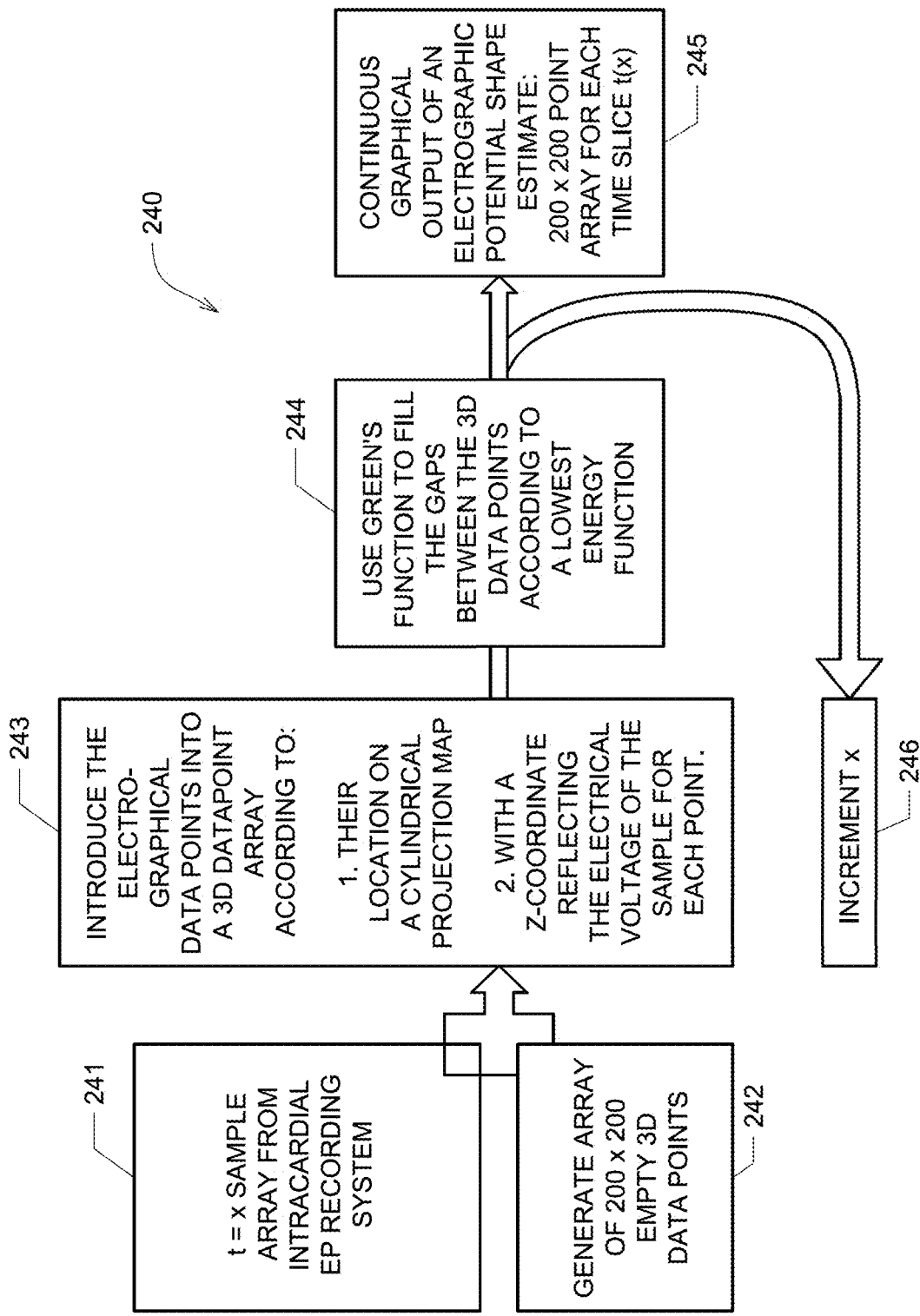
Figure 6C:
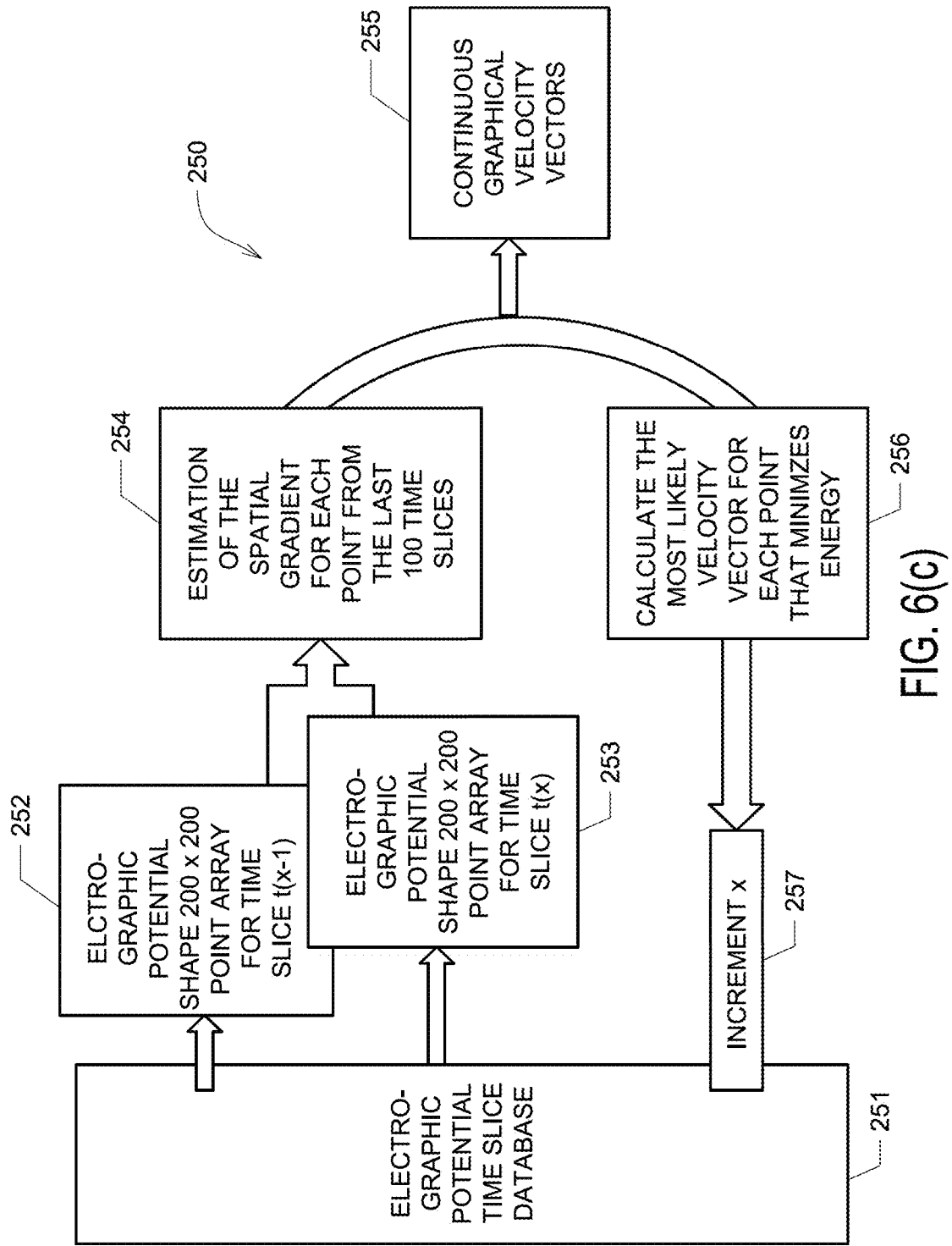

Referring now to FIGS. 6(*a*), 6(*b*) and 6(*c*), and with further reference to FIG. 4, there are shown some of the individual steps corresponding to the three main steps 230, 240 and 250 carried out according to one embodiment of algorithm 200 disclosed and described herein.

FIG. 6(*a*) shows one embodiment of steps 202 through 212 of main step 210 of FIG. 4 ("normalize/adjust amplitudes, filter electrogram signals). In FIG. 6(*a*), step 202 is shown as comprising receiving a data file corresponding to the EP recording of electrogram signals from a basket or other type of EP recording catheter positioned in a patient's heart 10. The time interval over which such electrogram signals are recorded inside the patient's heart 10 may, of course, vary according to, among other things, the requirements of the examination that is to be performed, and/or the suspected or known cardiac rhythm disorder from which the patient suffers, illustrative, but non-limiting, examples of such time intervals range between about a second and one minute or more. Bad or poor fidelity traces or electrograms may be selectively removed or edited at this stage.

At step 204, a high-pass filter is applied to the acquired EP data to remove DC offsets, as well as other undesirable low-frequency noise. In one embodiment, a 5 Hz high pass filter is applied, although other filters, including band-pass filters, are contemplated, including, but not limited to, 10 Hz high-pass filters, 5-20 Hz band-pass filters, and 5-50 Hz band-pass filters. Notch- and low-pass filtering may also be applied in step 204. Hanning, trapezoidal and other digital filtering and/or Fast Fourier Transform (FFT) filtering techniques may also be applied.

At step 206, an average far-field electrogram signal is generated by stacking and averaging all electrogram traces. In the case of atrial EP recordings, the resulting estimate of a far-field ventricular depolarization is subtracted from each trace individually, thereby removing or at least reducing the far-field component therefrom.

At step 208, the amplitudes of individual filtered electrogram signals are normalized with respect to a given standard deviation occurring over a predetermined time window (e.g., a moving window of 200 samples around a time value "x").

At step 212, a complete filtered sample array from the grid or basket catheter is provided as an output from first main step 210.

Referring now to FIG. 6(*b*), there is shown one embodiment of the second main step 230 of algorithm 200 shown in FIG. 4 (processing amplitude-adjusted electrogram signals across the 2D or 3D representation, map or grid to generate a plurality of three-dimensional electrogram surfaces, one surface being generated for each selected or predetermined discrete time or time slice).

In FIG. 6(*b*), second main step 240 is shown as including steps 241 and 243, which according to one embodiment are performed in parallel or near-parallel. At step 241, digitally sampled and processed electrogram signals from step 212 of FIG. 6(*a*) are provided, and at step 242 an array of 200×200 empty 3D data points are generated, which correspond to the 2D or 3D representation, map or grid which is to be generated (or has already been generated). In one embodiment, such a representation, map or grid is formed by making a cylindrical projection representation, map or grid that corresponds to an approximate estimate or calculated map of the region of the patient's myocardial wall where the electrogram signals were acquired and measured (see step 243) by catheter 110.

Positional data from Imaging or navigation system 70 can be provided at this stage to improve the positional accuracy of the individual locations with in such grid where electrogram signals were acquired. In one embodiment, for each time slice or sampled time, a Z-value or electrical potential corresponding to the normalized, adjusted and/or filtered measured voltage of each individual electrogram is assigned a location in the representation, map or grid.

At step 244, Green's function, or another suitable surface generating algorithm, is used to generate a surface of Z-values for each time slice or sampled time (more about which is said below). In one embodiment, the surface corresponding to the Z-values is smoothed.

At step 245, the calculated surface corresponding to each time slice or sampled time is provided as an output, with, for example, a 200×200 array of smoothed data points corresponding to the smoothed surface being provided for each time slice or sampled time. Note that in some embodiments the intervals at which time slices are selected, or the individual time slices themselves, may be predetermined, or may be selected automatically or by the user.

FIG. 6(*c*) shows step 250 corresponding to one embodiment of the third main step of FIG. 4 (processing the plurality of three-dimensional electrogram surfaces generated across a 2D or 3D map through time to generate a velocity vector map, for example by means of the optical flow analysis and estimation techniques and methods, such those described and disclosed elsewhere herein. In FIG. 6(*c*), third main step 250 is shown as including step 251, which in one embodiment entails sequentially accessing the individual surfaces generated for selected time slices and/or discrete times in step 240. At steps 252 and 253, adjacent time slices are analyzed and processed sequentially. In step 254, a spatial gradient corresponding to each point of the representation, map or grid is calculated say over, for example, the last 100 time slices. At step 255, a continuous graphical output of calculated flow vectors can be provided as a real-time or near-real-time output. At step 236, the most likely flow vector magnitude (or velocity) and direction for each point that minimizes energy is calculated. At step 257, X (or time) is incremented, and the foregoing calculations are repeated and refined, the final output of which is a vector velocity map of the type shown, by way of non-limiting example, in FIGS. 5(g), 7(e), 7(i), 7(j), 7(k), 7(l), 8, 9, 10(a), 10(c), and 10(e).

FIGS. 7(a) through 7(j) show the results of processing simulated atrial cardiac rhythm disorder data using the methods and techniques described and disclosed above, where the concept of analyzing complex rotor structures was applied to a data set of simulated data. The simulated data shown in FIG. 7(a) primarily comprised stable active and passive rotors, as described in Carrick et al. in "Prospectively Quantifying the Propensity for Atrial Fibrillation: A Mechanistic Formulation," R. T. Carrick, P. S. Spector et al.; Mar. 13, 2015, the entirety of which is hereby incorporated by reference herein. From Carrick, et al.'s video corresponding to the foregoing publication, and referring now to FIG. 7(a), stable rotor data were recorded for a frame delineated by the indicated blue square, where there are seven rotors. The recording was accomplished using the luminance of the video frame in an 8×8 matrix with an 8-bit signal depth, thereby to simulate electrogram signal data acquired using a conventional 64-electrode 8×8 basket catheter. The overall video comprised 90 frames. All data shown in FIG. 7(a) were taken from frame 60. Signal amplitudes from frame 60 are shown in the chess field and box plots of FIGS. 7(b) and 7(c), receptively.

Figure 7A:
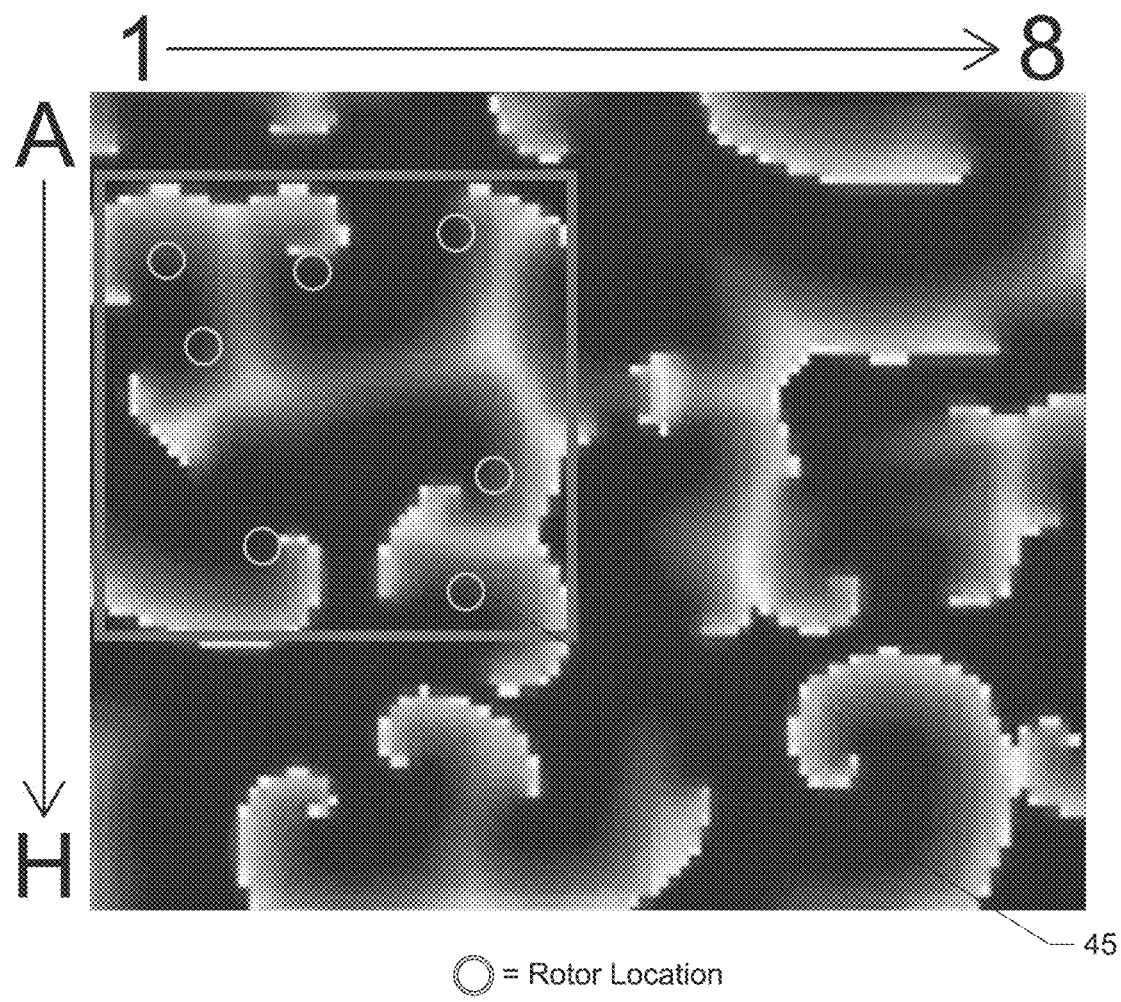
FIGS. 7(a) through 7(j) show the results of processing simulated atrial cardiac rhythm disorder data in accordance with one embodiment of method or algorithm 200.

In FIG. 7(a), 7 rotors are shown marked with circles with in the rectangle. In FIG. 7(b), a box plot of 8×8 matrix amplitudes is shown having amplitudes corresponding to frame 60. FIG. 7(d) shows the estimated wavefront or smoothed surface corresponding to frame 60. FIG. 7(c) shows the vector velocity map generated from the data corresponding to FIG. 7(a) (which was generated on the basis of all 90 frames or times slices). Reference to FIG. 7(e) shows that seven active rotors (marked with circles 45) are apparent, as are two passive rotors (marked with tars 46).

Figure 7B:
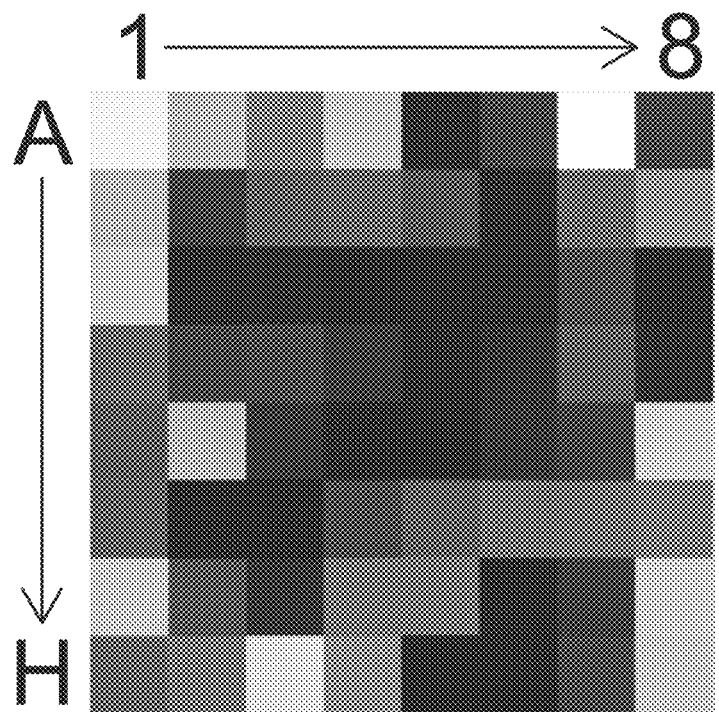
Figure 7C:
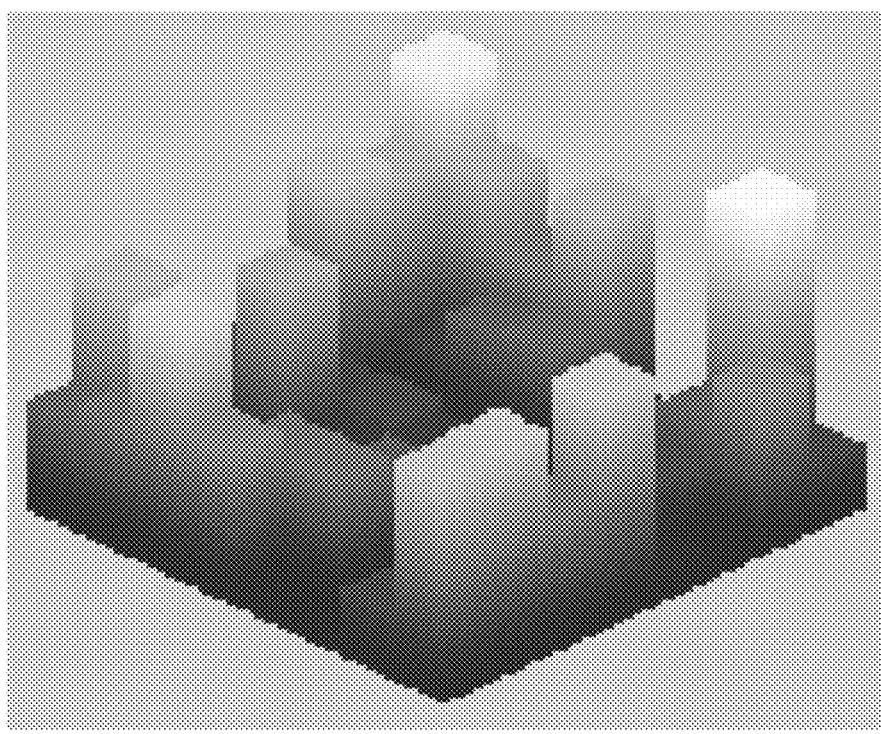
Figure 7D:
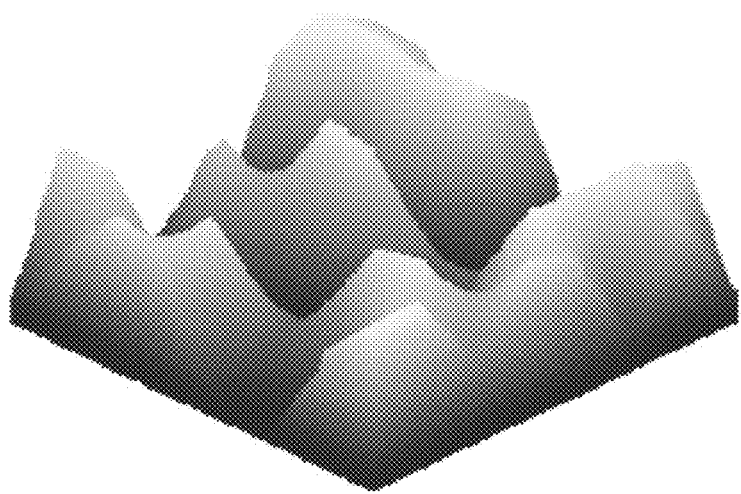
Figure 7E:
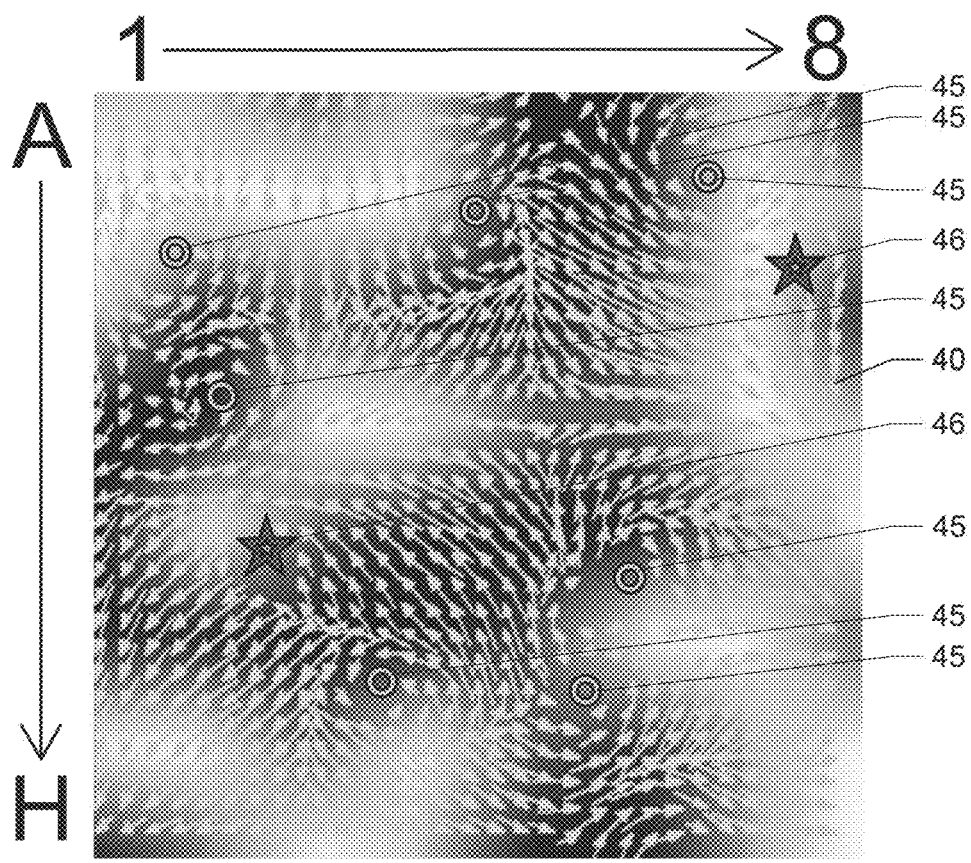

Referring now to FIGS. 7(b) and 7(c), it will be seen that the 2D and 3D box patterns shown therein provide rough estimates of the spatial wavefronts shown in FIG. 7(a), in FIG. 7(d), however, the original data shown in FIG. 7(a) are reproduced fairly accurately, and also provide a good input to the vector velocity map of FIG. 7(e) (which nicely reveals the 7 active rotors visible in FIG. 7(a)). The vector arrows 40 in FIG. 7(e) not only show the rotational centers of the individual rotors, but also show that active rotors indicated by circles 45 are driving sources of the wave fronts because the calculated vectors of the active rotors always point centrifugally away from the rotor centers, in contrast, the two stars 46 shown in FIG. 7(e) indicate the locations of passive rotors or flow turbulences that, while circular in shape, have centripetal vector directions to at least on one side of the rotor centers associated therewith.

Discrimination between active and passive rotors is critical to making proper therapeutic decisions regarding the delivery of ablation therapy, which should only target structures underlying the drivers of atrial fibrillation (namely, active rotors only, and not passive rotors).

Next, the effects of typical artifact disturbances on the signals of the 64 channels of data shown in FIGS. 7(a) through 7(d) were determined by introducing simulated variable amplitude DC-offset noise and artifacts into the electrogram signals. The objective was to test the extent to which such artifacts and noise might impair or disable the ability of algorithm 200 to detect rotors in the data.

Figure 7F:
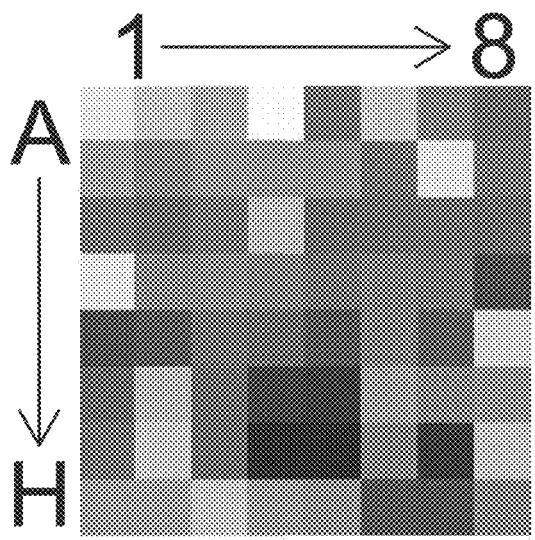
Figure 7G:
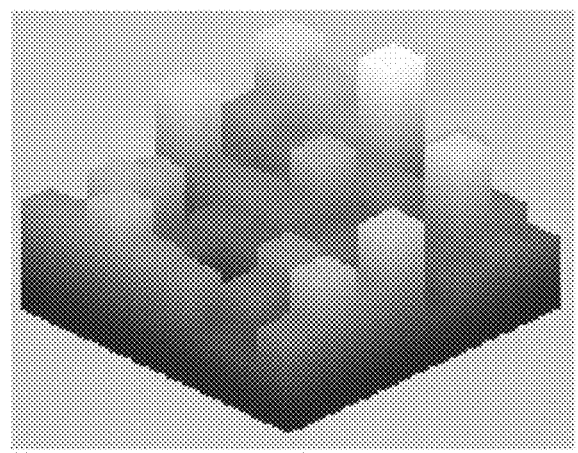
Figure 7H:
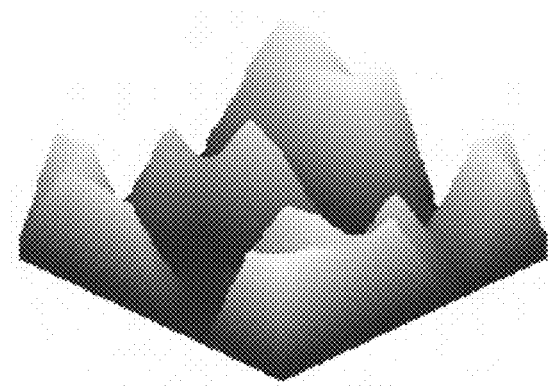

FIGS. 7(f) and 7(g) show the same box plot data as FIGS. 7(b) and 7(c), respectively, but with the foregoing-described superimposed and introduced artifacts. That is, FIGS. 7(f) and 7(g) show the chess field and box plots of the disturbed electrogram signals corresponding to frame 60. After filtering and normalization in slop 210, the original rotor structure shown in FIG. 7(a) once again becomes visible in FIG. 7(h) following completion of the main second step 240 of the algorithm.

Figure 7I:
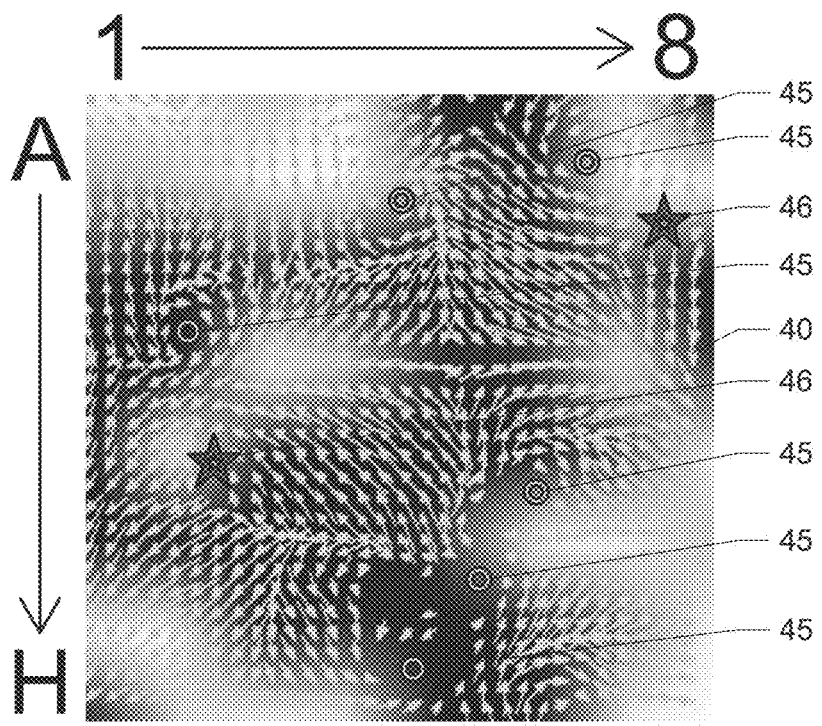

Upon applying smoothed surface calculations and fitting (as shown in FIG. 7(i)), algorithm 200 is seen to detect only five of the seven active rotors shown in FIG. 7(a). One additional active rotor, however, was detected at a different location (see FIG. 7(i)).

Figure 7J:
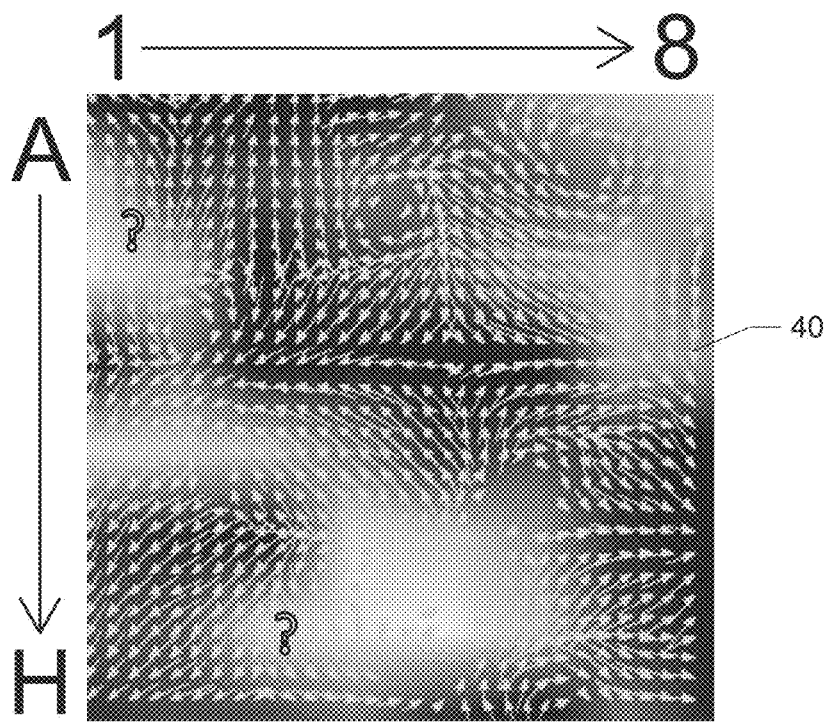

The largest variation in results was seen at positions where the introduction of the artifacts and noise reduced relative amplitude values by the greatest amount, as indicated by the white areas shown in FIG. 7(j). The white areas shown in FIG. 7(j) were generated by using the sliding-window amplitude-adjusted electrogram signal techniques described above, where electrograms processed using sliding-window techniques were used to generate the image background (including the white areas) shown in the velocity vector map of FIG. 7(j). The white areas in FIG. 7(j) thus correspond to low amplitude areas potentially indicative of valve defects or artifacts, loose electrode contact, and/or areas of fibrosis in the patient's myocardium. It is important to point out that the low-amplitude areas shown in white in the various velocity vector maps presented herein are not calculated using Green's function or optical flow data processing techniques. Instead, and as described above, these low-amplitude regions or areas may be detected by assessing the relative amplitudes of electrogram signals in step 210.

In the white areas of FIG. 7(j), the resulting velocity vector map shows that the active rotors indicated therein are slightly moved closer together than in FIG. 7(i), and on the left center side of FIG. 7(j) two rotors appearing in FIG. 7(i) are revealed as a single active rotor in FIG. 7(j). FIGS. 7(a) through 7(j) show that there are limits to the resolution that can be achieved using a conventional 8×8 array of sensing electrodes 82 in a basket catheter having standard inter-electrode spacing. Thus, higher electrode densities and more recording channels could increase the resolution and accuracy of the results obtained using algorithm 200.

After confirming that algorithm 200 was capable of detecting complex rotor structures accurately in a patient's myocardium—even in the presence of strong artifacts and noise—algorithm 200 was applied to different time portions of the actual patient data shown in FIG. 5(b) so as to test further the algorithm's efficacy and accuracy. A velocity vector map corresponding to data acquired between 4,700 milliseconds and 5,100 milliseconds in the original EP recording of FIG. 5(b) is shown in FIG. 8(a).

Figure 8A:
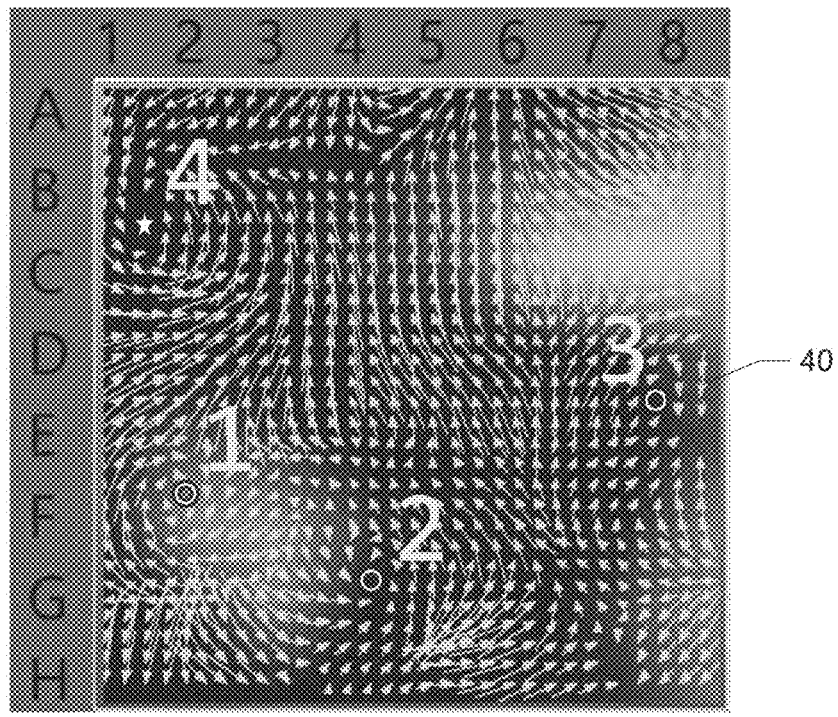
FIGS. 8(a) and 8(b) show velocity vector maps generated from actual patient data using different time windows and method or algorithm 200.

As shown in FIG. 8(a), four rotors indicated by circles 1, 2 and 3 and a star 4 were detected. Circles 1 and 2 in FIG. 8(a) appear to denote active rotors that are interacting with one another. Circle (3) in FIG. 8(a) may bean active rotor, but exhibits some centripetal components. Star 4 in FIG. 8(a) clearly corresponds to a passive rotor. Next, a velocity vector map corresponding to the same data set for data acquired between samples 0 seconds and 400 milliseconds was generated, the results of which are shown in FIG. 8(b).

Figure 8B:
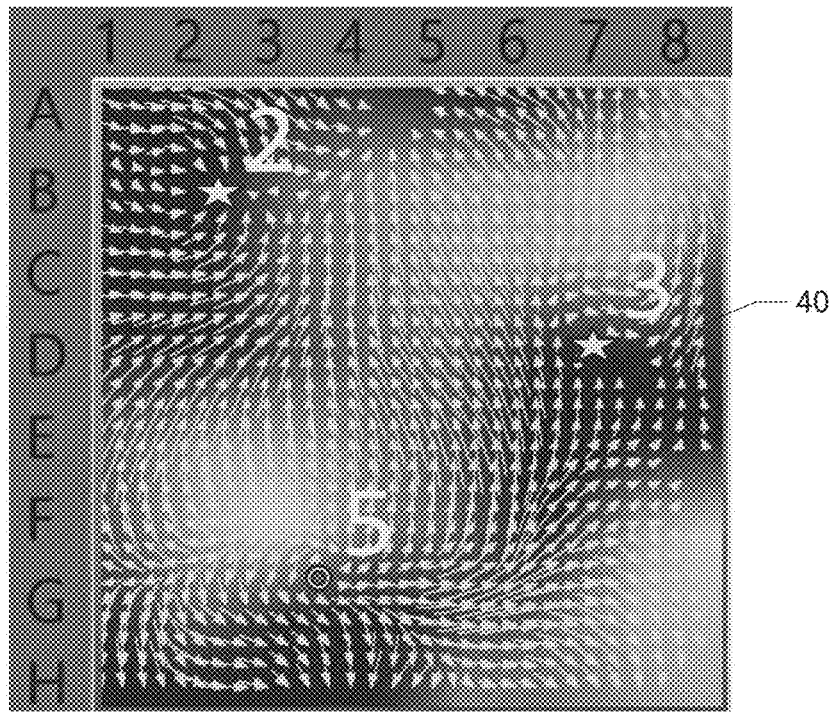

Differences between the results shown in FIGS. 8(a) and 8(b) permit a deeper insight into the true rotor structure of this patient's myocardium, as best shown in FIG. 8(b). In the earlier time interval (0 msec, to 400 msec.) of FIG. 8(b), the two associated rotors 1 and 2 shown in FIG. 8(a) are not yet active, while there is only a single active rotor 5 in FIG. 8(b) located between the positions of rotors 1 and 2 shown in FIG. 8(a). Rotors 1 and 2 in FIG. 8(b) show up at slightly different positions, but now appear clearly as passive rotors representing likely turbulences generated at the border of a mitral valve artifact.

Thus, a health care professional can select differing time windows over which to apply algorithm 200 to an EP mapping data set as a means of gaining a better understanding of the behavior of active and passive rotors, fibrotic regions, areas affected by valve defects or artifacts, breakthrough points and areas or defects that are at work in the patient's myocardium. The velocity vector maps generated by algorithm 200 permit a health care professional to identify such cardiac rhythm disorders in a patient's myocardium with a degree of precision and accuracy that has heretofore not been possible using conventional EP mapping and intravascular basket or spline catheter devices and methods.

Figure 9:
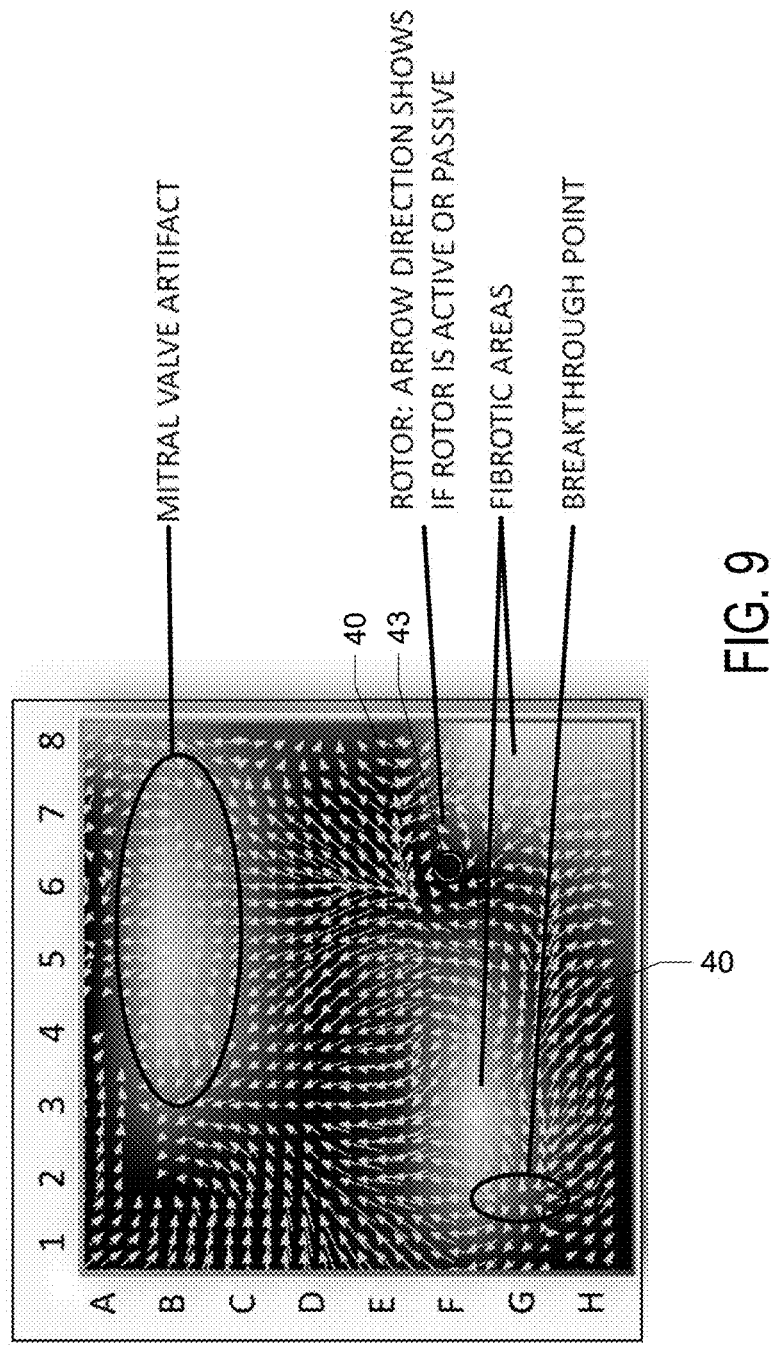
FIG. 9 shows another vector velocity map generated from actual patient data using method or algorithm 200.

Referring now to FIG. 9, there is shown another example of a vector velocity map generated from actual patient data using algorithm 200. In FIG. 9, the arrows 40 correspond to action potential wavefront velocity vectors, which is illustrated have differing magnitudes and directions associated herewith. As shown in FIG. 9, various cardiac rhythm defects and disorders become apparent as a result of the generated vector velocity map. The defects and disorders revealed by the vector velocity map of FIG. 9 include an active rotor (where the active rotor propagation direction is indicated in the bottom right of FIG. 9 by a circular arrow 43 rotating in a clockwise or centrifugal direction), a breakthrough point in the bottom left of FIG. 9, fibrotic areas indicted by low-amplitude white areas in the lower portion of FIG. 9, and a mitral valve defect indicted by the white area in the upper portion of FIG. 9.

Figure 10D:
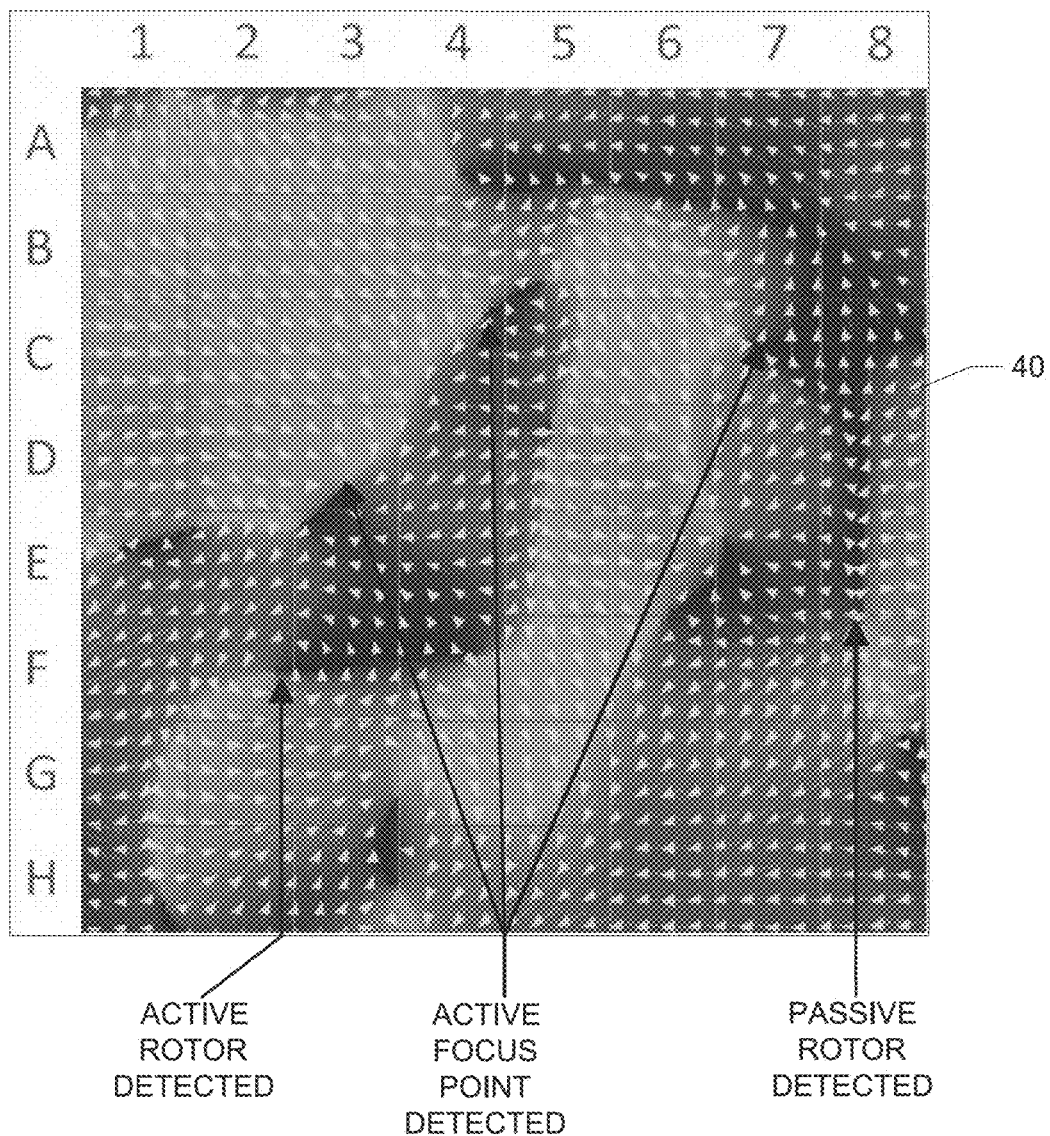

Referring now to FIGS. 10(a) through 10(d), there are shown further results obtained using the actual patient data. The raw data corresponding to FIGS. 10(a) through 10(d) were acquired from a single patient's right atrium using a 64-electrode basket catheter and corresponding EP mapping/recording system. Data were acquired at a 1 millisecond rate over a time period of 60 seconds in all 64 channels. FIGS. 10(a) and 10(b) correspond to one selected 2 second time window, and FIG. 10(d) corresponds to another time window from the same data set. FIG. 10(c) shows the greyscale-schemes employed in FIGS. 10(a), 10(b), and 10(d).

The vector velocity map of FIG. 10(a) generated using algorithm 200 clearly reveals an active rotor located at chess board position D/E, 213. The vector velocity map of FIG. 10(b) was also generated using algorithm 200, but using data acquired from only 16 electrodes 82 in grid D-C, 2-5. As shown in FIG. 10(b), the active rotor evident in FIG. 10(a) is nearly equally evident in FIG. 10(b) despite the significantly more sparse data grid employed to produce the velocity vector map. These remarkable results obtained using a sparse electrode grid are due in large part to the robustness, stability and accuracy of algorithm 200, as it has been applied to electrographical flow problems.

FIG. 10(d) shows another example of results obtained using algorithm 200 and EP mapping data obtained from the same patient as in FIGS. 10(a) and 10(b), but over a different time window. Note also that FIG. 10(d) shows that algorithm 200 has successfully detected one active rotor (at chess board location F2/3), three active focus points, and one passive rotor (at chess board location F8).

It will now be seen that algorithm 200 provides not only rotational direction information, but also provides high-resolution spatial information regarding the presence and location of rotors despite the use of sparse electrode grid spacing. Rotors can also move over time in a patient's myocardium, even during the time interval over which EP mapping is being carried out. The increased spatial and temporal resolution of algorithm 200 permits such shifts in rotor location to be detected.

In some embodiments, and as described above, multiple or different types of EP mapping and ablation catheters can be used sequentially or at the same time to diagnose and/or treat the patient. For example, a 64-electrode CONSTELLATION basket catheter can be used for EP mapping in conjunction with a PENTARAY 16- or 20-electrode EP mapping catheter, where the PENTARAY EP mapping catheter is used to zero in on, and provide fine detail regarding, a particular region of the patient's myocardium that the basket catheter has revealed as the location of a source of a cardiac rhythm disorder or irregularity. In addition, catheter 110 or any other EP mapping catheter used in system 100 may be configured to provide ablation therapy (in addition to EP mapping functionality). The various catheters employed in system 100 may also include navigation elements, coils, markers and/or electrodes so that the precise positions of the sensing, pacing and/or ablation electrodes inside the patient's heart 10 are known. Navigational data can be employed by computer 300 in algorithm 200 to provide enhanced estimates of the locations of the electrodes in the representations, maps or grids generated thereby, which in turn increases the accuracy and efficacy of the resulting velocity vector maps generated in algorithm 200.

In another embodiment, computing device/system 300 is operably connected to a storage medium such as a hard drive or non-volatile memory located in, or operably connected to, data acquisition device 140, where computing device 300 is configured to trigger an external switch operably connected to data acquisition device 140 which permits the upload of conditioned electrogram signal data from data acquisition device 140 to computing device 300. According to such a configuration, computing device 300 and data acquisition device 140 can remain galvanically isolated from one another, and the need to physically swap USB memory sticks between data acquisition device 140 and computing device 300 is eliminated. This, in turn, permits system 100 to operate more efficiently and quickly, and to provide vector velocity maps to the health care professional in near-real-time while the EP mapping procedure is being carried out within the patient's heart 10.

The various systems, devices, components and methods described and disclosed herein may also be adapted and configured for use in electrophysiological mapping applications other than those involving the interior of a patient's heart. These alternative applications include EP mapping and diagnosis of a patient's epicardium, a patient's spinal cord or other nerves, or a patient's brain or portions thereof.

It will now be seen that the various systems, devices, components and methods disclosed and described herein are capable of detecting with considerable accuracy and precision the locations of sources of cardiac rhythm disorders in a patient's heart.

What have been described above are examples and embodiments of the devices and methods described and disclosed herein, it is, of course, not possible to describe every conceivable combination of components or methodologies for purposes of describing the invention, but one of ordinary skin in the art will recognize that many further combinations and permutations of the devices and methods described and disclosed herein are possible. Accordingly, the devices and methods described and disclosed herein are intended to embrace all such alterations, modifications and variations that fall with in the scope of the appended claims. In the claims, unless otherwise indicated, the article "a" is to refer to "one or more than one."

The foregoing outlines features of several embodiments so that those skilled in the art may better understand the detailed description set forth herein. Those skilled in the art will now understand that many different permutations, combinations and variations of hearing aid 10 fall within the scope of the various embodiments. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

After having read and understood the present specification, those skilled in the art will now understand and appreciate that the various embodiments described herein provide solutions to long-standing problems, both in the use of electrophysiological mapping systems and in the use of cardiac ablation systems.

The invention claimed is:

1. A method of detecting a location of a source of at least one cardiac rhythm disorder in a patient's heart using at least one computing device and a display operably connected thereto, where the at least one computing device comprises at least one non-transitory computer readable medium configured to store instructions executable by at least one processor for determining the source and location of the cardiac rhythm disorder in the patients heart, the method comprising:
   (a) receiving a plurality of electrogram signals from an array of plurality of electrodes positioned in or on a patient;
   (b) in the computing device, assigning spatial or areal positions of electrodes to each of the plurality of electrodes and to each of the individual electrogram signals corresponding to each electrode;
   (c) for each or selected discrete times over which the plurality of electrogram signals are being processed, processing the plurality of electrogram signals in the computing device to generate a plurality of three-dimensional electrogram surfaces or data sets corresponding at least partially to the electrode positions;
   (d) processing the plurality of three-dimensional electrogram surfaces or data sets through time in the computing device to generate a vector map or visualization corresponding at least partially to the electrode spatial or areal positions, the vector map or visualization being configured to reveal the location of the source of the at least one cardiac rhythm disorder, and
   (e) displaying to a user on the display the vector map or visualization.

2. The system of claim 1, further comprising normalizing and/or adjusting amplitudes of the plurality of electrogram signals in the data acquisition device before processing the plurality of electrogram signals in the computing device to generate the plurality of three-dimensional electrogram surfaces or data sets corresponding at least partially to the electrode positions.

3. The system of claim 1, wherein one surface or data set is generated for each time when the plurality of three-dimensional electrogram surfaces or data sets is generated.

4. The system of claim 1, wherein at least portions of the electrogram surfaces or data sets generated by the computing device are configured to correspond to estimated wave shapes or wavefront.

5. The system of claim 1, wherein the electrogram surfaces or data sets are generated by the computing device using at least one of Green's function and a two-dimensional bi-harmonic spline interpolation function.

6. The system of claim 1, wherein the vector map or data sets generated by the computing device comprise arrows or colors representative of directions of electrical potential propagation.

7. The system of claim 1, wherein the vector map or data sets generated by the computing device comprise arrows or colors having attributes representative of velocities of electrical potential propagation.

8. The system of claim 1, wherein the vector map or data sets generated by the computing device are configured to reveal the at least one cardiac rhythm disorder as one or more of an active rotor at the location, a passive rotor at the location, a focal point at the location, and a breakthrough point at the location.

9. The system of claim 1, wherein a velocity vector map is generated by the computing device using at least one optical flow analysis technique.

10. The system of claim 9, wherein the at least one optical flow analysis technique is selected from the group consisting of a Horn-Schunck method, a Buxton-Buston method, a Black-Jepson method, a phase correlation method, a block-based method, a discrete optimization method, a Lucas-Kanade method, and a differential method of estimating optical flow.

11. The system of claim 1, wherein the plurality of electrogram signals are processed by the computing device to generate an averaged electrogram signal, and the averaged electrogram signal is subtracted from each of the individual electrogram signals to generate artifact- or far-field adjusted individual electrogram signals.

12. The system of claim 11, wherein the artifact-adjusted individual electrogram signals are processed by the computing device with a high-pass filter to remove DC offsets.

13. The system of claim 11, wherein the high-pass filter applied by the computing device removes frequencies below between about 5 Hz and about 20 Hz.

14. The system of claim 1, wherein interpolated or estimated values are generated by the computing device for positions in between the spatial or areal positions of the electrodes or their corresponding electrogram signals.

15. The system of claim 1, wherein a representative amplitude value is generated by the computing device for each individual electrogram signal, and the representative amplitude value generated for each electrogram signal is stored for later use in image backgrounds that show low signal amplitude areas, the low signal amplitude areas being indicative of one or more of valve artifacts, poor electrode contact, and fibrotic areas of the heart.

16. The system of claim 1, wherein the spatial or areal positions of the electrodes or their corresponding electrogram signals are modified by the computing device based upon navigational or positional data corresponding to measured or sensed actual electrode positions.

17. The system of claim 16, wherein interpolated or estimated values are generated by the computing device for positions in between the spatial or areal position of the electrodes or their corresponding electrogram signals.

18. The system of claim 16, wherein the navigational data are provided to the computing device by one or more of a medical navigation system, a computed tomography scanner, a magnetic resonance image scanner, and an X-ray fluoroscopy system.

19. The system of claim 1, further comprising an ablation system comprising an ablation catheter, the ablation catheter being configured for ablating the patient's heart at a location of a source of the cardiac rhythm disorder indicated by the vector map.

* * * * *